United States Patent [19]

Tarasewicz et al.

[11] Patent Number: 5,789,389
[45] Date of Patent: Aug. 4, 1998

[54] BCL2 DERIVED GENETIC ELEMENTS ASSOCIATED WITH SENSITIVITY TO CHEMOTHERAPEUTIC DRUGS

[75] Inventors: Dariusz G. Tarasewicz. Lisle; Brigitte Schott, Chicago, both of Ill.; Tatyana A. Holzmayer, Palo Alto, Calif.; Igor B. Roninson, Wilmette, Ill.

[73] Assignee: Board of Trustees of University of Illinois, Urbana, Ill.

[21] Appl. No.: 405,702

[22] Filed: Mar. 17, 1995

[51] Int. Cl.$^6$ ............................................. A01N 43/04
[52] U.S. Cl. ............................................. 514/44; 536/24.5
[58] Field of Search ............................. 536/24.5, 23.1, 536/25.3; 514/44; 435/91.1

[56] References Cited

U.S. PATENT DOCUMENTS

| | | | |
|---|---|---|---|
| 5,015,568 | 5/1991 | Tsujimoto et al. | 435/5 |
| 5,217,889 | 6/1993 | Roninson et al. | 435/172.3 |

OTHER PUBLICATIONS

Orkin, et al. 1995, "Report and Recommendations of the Panel to Assess the NIH Investment in Research on Gene Therapy".
Gura, T. 1995. Science. vol. 270. pp. 575–577. "Antisense Has Growing Pains".

*Primary Examiner*—Nancy Degen
*Assistant Examiner*—Irene Yucel
*Attorney, Agent, or Firm*—McDonnell Boehnen Hulbert & Berghoff

[57] ABSTRACT

The invention provides genetic suppressor elements that are derived from the apoptosis-related gene BCL2. The invention provides genetic suppressor elements that are capable of inhibiting BCL2 gene expression and BCL2-mediated suppression of apoptosis in mammalian cells. The GSEs provided by the invention are also useful for sensitizing cancer cells to the cytotoxic effects of chemotherapeutic drugs. The invention provides methods for identifying and obtaining such elements, and therapeutic methods of using such elements for treatment of cancer cells and animals bearing malignant tumors.

4 Claims, 14 Drawing Sheets

FIG. 1

5' Adaptor

HindIII

```
5' T A C C G A A T T C A A G C T T A T G G A T G G A T G      SEH
       C T T A A G T T C G A A T A G C T A C C T A C 5'  ASEH
```

3' Adaptor

ClaI

```
5' T G A G T G A G T G A A T C G A T G G A T C C              SCB
       A C T C A C T C A C T T A G C T A C C T A G G A T A T 5'  ASCB
```

FIG. 2

```
AGTGGATG GA C G    (single ATG adaptor)

AGTGGATG GA C      (frameshift adaptor)

ATGG ATG GA|T G|TG GTC CAC CTG ACC CTC CGC CAG GCC GGC GAC GAC TTC TCC
      M   D  |V   V   H   L   T   L   R   Q   A   G   D   D   F   S
5' adaptor    |
```

```
CGC CGC TAC CGC CGC GAC TTC GCC GAG ATG TCC AGC CAG C|TG| AGT GAG TGC
                                        C       T
 R   R   Y   R   R   D   F   A   E   M   S   S   Q   L    S   E   ---
                                        T       C
mutations                             2-25    6-2        3' adaptor
``` hours after VCR treatment

Hrs after VCR

BCL2 DERIVED GENETIC ELEMENTS ASSOCIATED WITH SENSITIVITY TO CHEMOTHERAPEUTIC DRUGS

BACKGROUND OF THE INVENTION

This invention was made with support under Grant Nos. 1-R01-CA62099 and 2-R37-CA40333 from the National Institutes of Health. The government has certain rights in this invention.

FIELD OF THE INVENTION

The invention relates to genetic factors associated with apoptosis and sensitivity to chemotherapeutic drugs. More particularly, the invention relates to methods for identifying such factors as well as to uses for such factors. The invention specifically provides genetic suppressor elements derived from mammalian BCL2 genes, and therapeutic uses related thereto.

SUMMARY OF THE RELATED ART

Cancer remains one of the leading causes of death in the United States. Clinically, a broad variety of medical approaches, including surgery, radiation therapy and chemotherapeutic drug therapy are currently being used in the treatment of human cancer (see the textbook *CANCER: Principles & Practice of Oncology*, 4th Edition, De Vita et al., eds., J. B. Lippincott Company, Philadelphia, Pa., 1994). However, it is recognized that such approaches continue to be limited by a fundamental lack of a clear understanding of the precise cellular bases of malignant transformation and neoplastic growth.

The beginnings of such an understanding of the cellular basis of malignant transformation and neoplastic growth have been elucidated over the last ten years. Growth of normal cells is now understood to be regulated by a balance of growth-promoting and growth-inhibiting genes (see Varmus, 1989, "A historical overview of oncogenes", in *Oncogenes and the Molecular Origin of Cancer*, Weinberg, ed., Cold Spring Harbor Press, Cold Spring Harbor, N.Y., pp. 3–44). Cancer, which results in part due to an imbalance between the action of these two types of genes, can be viewed as a deregulation in the normal homeostasis that occurs between cellular proliferation and active cell death (ACD), otherwise known as apoptosis or programmed cell death (Hoffman et al., 1994, *Oncogene* 9: 1807–1812). The main emphasis in cancer research has been traditionally placed on identifying the genetic events that lead to increased cellular proliferation in cancer. In the past few years, however, more attention has been paid to understanding the altered patterns of cell death that exist in cancer.

Active cell death (ACD) is a process that is present in numerous physiological systems. It plays a role in such diverse events as clearance of cells during embryonic differentiation, destruction of neurons after growth factor withdrawal and molding of the immune repertoire in mammals (see Hoffman et al., ibid.; Ellis and Horwitz, 1986, *Cell:* 44: 817–829; Wyllie, 1994, *Nature* 369: 272–273). One gene which plays a general role in the process of ACD in different systems is the proto-oncogene BCL2. Originally this gene was found to be involved in translocations occurring in many non-Hodgkin's lymphomas (Tsujimoto and Croce, 1986, *Proc. Natl. Acad. Sci. USA* 83: 5214–5218). It was subsequently discovered that BCL2, when overexpressed, can prevent ACD triggered by various physiological stimuli (Reed, 1994, *J. Cell Biol.* 124: 1–6). In the case of lymphomas, where BCL2 was activated by translocation, this block of ACD results in abnormal proliferation of lymphoid cells.

The exact mechanism of anti-apoptotic activity of BCL2 has not yet been firmly established. It is known, however, that BCL2 interacts, physically and functionally, with several other proteins, some of which (such as BAX) are structurally related to BCL2 (Reed, 1994, ibid.). Recent studies on clinical samples demonstrated that expression of BCL2 is not confined to hematological malignancies: BCL2 is expressed in a high percentage of colorectal, brain, prostate and lung tumors (see Hague et al., 1994, *Oncogene* 9: 3367–3370; Leek et al., 1994, *Brit. J. Cancer* 69: 135–139; McDonnell et al., 1994, *Cancer Res.* 52: 6940–6944; Pezzella et al., 1993, *New Engl. J. Med.* 329: 690–694; Miyashita and Reed, 1992, *Cancer Res.* 52: 5407–5411). These findings suggest that BCL2 plays a widespread role in human cancers.

It has also become apparent that ACD plays a central role in cancer chemotherapy. Many commonly used chemotherapeutic agents induce ACD in tumor cells. While these drugs injure the cell in different ways (i.e., DNA damage, microtubule fixation, hormone ablation, etc.), the induction of ACD is the common phenomenon which is ultimately responsible for the cytotoxicity of these anticancer drugs. BCL2 has been shown to inhibit ACD induced by different classes of anticancer drugs. Several studies demonstrated that tumor cells made to overexpress BCL2 after transfection of full-length BCL2 cDNA developed resistance to the cytotoxic effects of a number of different drugs (see Miyashita and Reed, ibid; Kamesaki et al., 1993, *Cancer Res.* 53: 4251–4256; Miyashita and Reed, 1993, *Blood* 81: 151–157), as determined under conditions of transient but not continuous drug exposure.

Thus, inhibitors of BCL2 could have significant potential applications for sensitization of different malignancies to chemotherapeutic treatment or direct growth inhibition. Antisense RNA technology has been used to attempt to create specific inhibitors of BCL2. Chemically modified oligodeoxynucleotides complementary to BCL2 mRNA, or antisense BCL2 RNA expressed in cells via plasmid expression vectors have been shown to have growth-inhibitory (Reed et al., 1990, *Cancer Res.* 50: 6565–6570; Reed et al., 1990, *Proc. Natl. Acad. Sci. USA* 87: 3660–3664) and drug-sensitizing (Kitada et al., 1993, *Antisense Res. Devel.* 3: 157–169; Kitada et al., 1994, *Antisense Res. Devel.* 4: 71–79) effects on BCL2-expressing cells in vitro. The specificity of antisense reagents and their efficacy under in vivo conditions have not been determined. No other types of genetic or chemical inhibitors of BCL2 have yet been reported.

U.S. Pat. No. 5,015,568 to Tsujimoto and Croce disclose isolated nucleic acids and methods of use thereof comprising the protein coding regions of the human BCL2 gene.

U.S. Pat. No. 5,202,429 to Tsujimoto and Croce disclose isolated cDNA encoding human BCL2 gene and uses thereof.

International Patent Application, Publication No. WO91/15155 to Cory et al. disclose transgenic non-human animals bearing human BCL2 transgenes.

International Patent Application, Publication No. WO94/27426 to Reed disclose methods of treating a disease or disorder comprising increasing the activity of BCL2 in the cells of a tissue or organ in an animal, and describe a truncated version of the BCL2 protein having dominant negative mutant activity.

Tsujimoto and Croce, 1986, ibid. teach the isolation and characterization of a cDNA clone encoding human BCL2.

Seto et al., 1988, EMBO J. 7: 123–131 disclose the genomic DNA structure of the human BCL2 gene in germline and translocated embodiments.

Reed et al., 1990, ibid. disclose antisense inhibition of BCL2 gene expression in leukemic cells using oligonucleotides specific for a region surrounding the ATG initiator codon.

Reed et al., 1990, ibid. disclose antisense inhibition of BCL2 gene expression in leukemic cells using full-length and truncated antisense copies of BCL2 cDNA.

McDonnell et al., 1992, ibid. teach the association of BCL2 expression with androgen-independent prostate cancer.

Miyashita and Reed, 1992, ibid. teach that expression of functional BCL2 cDNA expression constructs in murine lymphoid cells increases resistance to glucocorticoid- and chemotherapeutic drug-induced cell death.

Kamesaki et al., 1993, ibid. teach BCL2-mediated resistance to etoposide.

Miyashita and Reed, 1993, Blood, ibid. teach that BCL2 mediates blockage of apoptosis in human 697 leukemia cells.

Kitada et al., 1993, ibid., disclose antisense RNA-mediated reduction of BCL2 gene expression.

Kitada et al., 1994, ibid., disclose reduction of BCL2 gene expression in lymphoma cells and reducing chemoresistance thereby.

Reed, 1994, ibid. provides a review of the role of BCL2 in cancer and active (or programmed) cell death.

Sato et al., 1994, Proc. Natl. Acad. Sci. USA 91: 9238–9242 disclose protein-protein binding interactions among BCL2 and other members of the BCL2 protein family.

Boyd et al., 1994, Cell 79: 341–351 disclose that adenovirus protein E1B and human BCL2 protein interact with a common set of cellular proteins.

Cotter et al., 1994, Oncogene 9: 3049–3055 disclose antisense oligonucleotides comprising the initiator ATG codon of BCL2 inhibit B-cell lymphoma growth in vivo in SCID-hu mice.

Milligan et al., 1994, Annals of N.Y. Acad. Sci. 716: 228–241 review antisense-based modalities of cancer therapy.

The discovery and analysis of new inhibitors of BCL2 gene function may be greatly accelerated through the use of genetic suppressor elements (GSEs), which may be derived from a BCL2 gene and be capable of selectively suppressing its function. GSEs are short gene fragments that interfere with expression or function of a gene in a cell. Such GSEs confer upon cells expressing or comprising them a phenotype for the loss-of-gene function of the gene to which the particular GSE corresponds. Recently, some developments have been made in the difficult area of isolating GSEs and their cognate recessive genes using GSE technology. Roninson et al., U.S. Pat. No. 5,217,889 (issued Jun. 8, 1993) teach a generalized method for obtaining GSEs (see also Holzmayer et al., 1992, Nucleic Acids Res. 20: 711–717). Co-pending U.S. National Phase patent application 08/039,385, filed Sep. 7, 1993, corresponding to International Application PCT/US91/07942, filed Oct. 11, 1991, and Gudkov et al., 1993, Proc. Natl. Acad. Sci. USA 90: 3231–3235 teach isolation of GSEs from topoisomerase II cDNA that induce resistance to topoisomerase II-interactive drugs. Co-pending U.S. patent application Ser. Nos. 08/033,986, filed Mar. 3, 1993, and Ser. No. 08/177,571, filed Jan. 5, 1994, disclosed the discovery by the present inventors of the novel and unexpected result that GSEs isolated from RNA of cells resistant to the anticancer DNA damaging agent etoposide, include a GSE encoding an antisense RNA homologous to a portion of a kinesin heavy chain gene. Additionally, co-pending U.S. patent application Ser. No. 08/033,986 disclosed two other GSEs from previously-unknown genes, the expression of said GSEs conferring etoposide resistance on mammalian cells. Co-pending U.S. patent application Ser. No. 08/199,900, filed Feb. 22, 1994, disclosed GSEs from previously-unknown genes, the expression of said GSEs conferring cisplatin resistance on mammalian cells. Finally, co-pending U.S. patent application Ser. No. 08/204,740 disclosed GSEs that immortalized, or that immortalized and neoplastically transformed, primary mammalian embryo fibroblasts in vivo and in vitro.

These results further underscored the power of the GSE technology developed by these inventors to elucidate recessive gene-mediated biological phenomenon involving unexpected mechanisms, including drug resistance in cancer cells and oncogenic transformation, thereby providing the opportunity and the means for overcoming drug resistance in cancer patients. This technology has now been applied to isolating and identifying GSEs specific for BCL2 that sensitize cells expressing the BCL2 proto-oncogene to the cytotoxic effects of chemotherapeutic drugs, and GSEs that are capable of inducing or facilitating active cell death in such BCL2-expressing cells.

BRIEF SUMMARY OF THE INVENTION

The invention provides genetic suppressor elements (GSEs) that are fragments derived from a gene, BCL2, that is associated with active cell death (ACD, also known as apoptosis) in mammalian cells. The invention specifically provides GSEs derived from cDNA and genomic DNA encoding the BCL2 gene, and methods for producing such GSEs from BCL2 gene sequences. As this gene is also associated with sensitivity to chemotherapeutic drugs, and can confer resistance to chemotherapeutic drugs and DNA damaging agents, GSEs are provided by the invention that confer upon cancer cells sensitivity to chemotherapeutic drugs and that have antineoplastic properties themselves. Therapeutic methods and pharmaceutical compositions of the GSEs of the invention are also provided. The invention also provides a method for identifying and isolating GSEs derived from BCL2 that confer sensitivity to chemotherapeutic drugs. This method utilizes transient exposure to chemotherapeutic or cytotoxic drugs of cells that harbor clones from a random fragment expression library derived from BCL2-specific cDNA, and subsequent rescue of library inserts from cells preferentially undergoing active cell death as a consequence of such exposure.

In a first aspect, the invention provides a sense-oriented genetic suppressor element for reversing BCL2-mediated suppression of apoptosis in a mammalian cell. In this embodiment of the invention are provided nucleic acids encoding a peptide having an amino acid sequence that is a portion of the BCL2 amino acid sequence. In particular embodiments, such an amino acid sequence optionally in addition encodes a methionine residue, a glutamic acid residue, or the sequence Met-Glu or Glu-Met at the amino terminus of the peptide. In other particular embodiments, the amino acid sequence optionally in addition encodes a serine residue, an aspartic acid residue, or the sequence Ser-Asp or Asp-Ser at the carboxyl terminus of the peptide. In yet other particular embodiments, the amino acid sequence of the BCL2-derived GSE-encoded peptides of the invention optionally in addition encodes a methionine residue, a glutamic acid residue, or the sequence Met-Glu or Glu-Met at the amino terminus of the peptide, and wherein the amino acid sequence of the peptide optionally in addition encodes a serine residue, an aspartic acid residue, or the sequence Ser-Asp or Asp-Ser at the carboxyl terminus of the peptide. Preferred embodiments of GSE-encoded peptides provided by this aspect of the invention are identified as SEQ ID Nos.: 6, 8 and 10.

Also provided by this aspect of the invention are sense-oriented genetic suppressor elements for reversing BCL2-mediated suppression of apoptosis in a mammalian cell comprising nucleic acids wherein the amino acid encoded by the GSE is modified by replacement or substitution of an amino acid in the sequence of the encoded peptide. In these embodiments of the invention, the GSE comprises an amino acid sequence wherein an amino acid residue at a position in the sequence is different from the amino acid residue found at that position in the sequence of the mammalian BCL2 gene from which the GSE is derived. Such amino acid substitution GSEs comprise both naturally-occurring and man-made substitutions or replacements in the amino acid sequence.

Also provided by this aspect of the invention are synthetic peptides having an amino acid sequence encoded by the nucleic acid of the BCL2 GSEs of the invention comprising from about 6 amino acids to all of the amino acid sequence encoded by the genetic suppressor element of the invention.

In a second aspect, the invention provides methods of reversing BCL2-mediated suppression of apoptosis in a cell. In particular embodiments of this aspect of the invention are provided reagents, including pharmaceutical compositions, of the GSEs and GSE-encoded peptides of the invention, and synthetic embodiments thereof. Particular uses of the methods provided by this aspect of the invention comprise sensitizing a cancer cell to a chemotherapeutic agent. Other useful embodiments of the methods provided by this aspect of the invention comprise methods for treating an animal having a malignant tumor or malignant cells in the animal's body. Yet other useful embodiments include methods for increasing apoptosis in a cell, in vivo or in vitro. Each of these methods comprise steps of introducing into a cell a GSE or GSE-encoded peptide of the invention, or synthetic embodiments thereof. For in vivo and therapeutic uses, pharmaceutical compositions of the GSEs and GSE-encoded peptides of the invention are provided. In particular embodiments, such pharmaceutical compositions also comprise a therapeutically-effective amount of a cytotoxic or chemotherapeutic agent or combination of such agents.

In a third aspect, the invention provides BCL2 GSEs having optimized anti-BCL2 activity, and methods for obtaining GSEs having such optimized anti-BCL2 activity. In one embodiment of such methods are utilized the detection of active cell death by transient cytotoxic drug treatment of cells that harbor clones from a random fragment expression library derived from DNA of a BCL2 gene. In such embodiments, anti-BCL2 GSEs are rescued following transient cytotoxic treatment by specific detection of apoptotic (i.e., dead or dying) cells, by isolation of the library inserts therefrom. Particularly and preferably provided are such optimized GSEs derived from human BCL2 (SEQ ID Nos.: 11 & 12).

In a fourth aspect are provided methods of use of the BCL2-derived GSEs of the invention as anticancer agents per se and as agents for sensitizing cancer cells to the cytotoxic effects of chemotherapeutic drugs. In particular embodiments of this aspect of the invention are provided methods for sensitizing cancer cells to a chemotherapeutic agent. Another embodiment of this aspect comprises a method of treating an animal having a malignant tumor or malignant cells in the animal's body. In yet another embodiment, a method is provided for increasing apoptosis in a cancer cell. Each of these methods of the invention comprise steps of introducing into the cancer cell a genetic suppressor element of the invention or, in the alternative, contacting the cancer cell with a synthetic peptide or oligonucleotide embodiment of the BCL2-derived GSE of the invention.

In a fifth aspect, the invention provides a method of identifying a genetic suppressor element derived from a BCL2 gene that is capable of increasing the sensitivity of cancer cells to one or more chemotherapeutic agent. The method provided by the invention comprises the steps of: (a) generating a set of random fragments of a cDNA encoding the BCL2 gene; (b) transferring the DNA fragments to an expression vector to yield a library, wherein the expression vector is capable of expressing the DNA fragments in a living cell; (c) genetically modifying living cells by introducing the random fragment library of step (b) into the living cells; (d) transiently exposing the genetically modified cells of step (c) to a cytotoxic agent; (e) isolating a subpopulation of dead or dying cells from the population of genetically-modified cells of step (d); and (f) obtaining the genetic suppressor elements from the subpopulation of genetically modified cells of subpart (e). The invention also provides sense-oriented and antisense-oriented GSEs identified by this method, and synthetic peptides and oligonucleotides having an amino acid or nucleotide sequence, respectively, of the GSEs identified by the method of the invention. In preferred embodiments, the random fragment library is produced in a retroviral expression vector construct capable of expressing the DNA fragments in a living cell.

This invention provides GSEs that are small, readily-produced peptides having an amino acid sequence derived from BCL2. The peptides of the invention include linear and cyclized peptides and substitution and addition variants thereof. For substitution variants, amino acid residues at one or more positions in such GSE-encoded peptides are replaced with a different amino acid residue (including atypical amino acid residues) from that found in the corresponding position of the BCL2 protein from which the specific peptide is derived. For addition variants, peptides may include additional amino acids, covalently linked to either the amino-terminal or carboxyl-terminal extent, or both, of the BCL2 GSE-encoded peptides herein described. Such additional amino acids may duplicate amino acids in BCL2 contiguous to the sequence comprising the GSE or may be unrelated to BCL2 amino acid sequences and may include atypical amino acids. In addition, GSE-encoded peptides of the invention may be provided as fusion proteins with other functional targeting agents, such as immunoglobulin fragments. Other variants include derivatives and modifications of amino acid side chain chemical groups such as amines, carboxylic acids, alkyl and phenyl groups.

Particularly provided are synthetic embodiments of the GSE-encoded peptides of the invention, covalently linked with or fused to virally-derived polypeptides or peptide fragments of such viral polypeptides, wherein the virally-derived portion of the fusion peptide enables the efficient introduction of the GSE-encoded peptides of the invention into intact cells. In preferred embodiments of these fusion proteins, the virally-derived portion of the fusion peptide is a homolog of the tat gene of human lentiviruses such as human immunodeficiency viruses.

The GSEs provided by the invention have, inter alia, utility as agents for sensitizing tumor cells to anticancer agents. Such anticancer agents include the drugs tested herein as described below, as well as many other cytotoxic drugs and ionizing radiation. Another utility of the GSEs of the invention are as anticancer agents per se, as BCL2 is known to act as an oncogene (cancer-causing gene) in certain malignancies, including non-Hodgkin's lymphomas and B-cell malignancies.

The GSEs provided by the invention also have, inter alia, utility as agents for increasing apoptosis in mammalian cells. Specific applications for such apoptotic agents include treatment of cells harboring cytopathic viruses; treatment of embryonic, fetal, or developing cells, particularly developing hematopoietic cells, having apoptosis-related disorders or abnormalities in their developmental programming; treatment of neurological disorders related to inappropriate apoptosis; and other apoptosis-related diseases or disorders in an animal. Reagents and compositions, particularly pharmaceutical compositions, are also provided by this invention for use in such methods. Methods and reagents for inhibiting apoptosis-mediated senescence and cell death as well are provided by the invention.

The invention specifically provides methods and reagents for reducing BCL2 gene expression in a cell expressing the BCL2 gene. In preferred embodiments, reagents of the invention useful in such methods comprise introducing into a cell expressing a BCL2 gene, a GSE or GSE-encoded peptide of the invention. In additional preferred embodiments, the invention provides methods for inhibiting the function of a BCL2 gene product in a cell expressing BCL2. In yet additional preferred embodiments, the invention provides methods for inhibiting BCL2 gene expression.

The invention also provides recombinant expression constructs, and cells carrying such recombinant expression constructs, wherein such constructs are capable of directing the expression of GSEs of the invention in cells carrying them.

The invention provides pharmaceutical compositions of the GSEs of the invention for use in cancer chemotherapeutic protocols and as anticancer agents per se for certain malignancies. The pharmaceutical compositions comprise unit dosages of the BCL2-derived GSE-encoded peptides of this invention in solid, semi-solid and liquid dosage forms such as tablet pills, powder, liquid solution or suspensions and injectable and infusible solutions. The invention also provides pharmaceutical compositions of the GSE-encoded peptides or combinations of the GSE-encoded peptides of the invention in a pharmaceutically-acceptable carrier or diluent. In such formulations, the GSE-encoded peptides of the invention are provided both per se and in combination with other anticancer agents. Methods of using these pharmaceutical compositions for the treatment of malignancies in a mammal, including humans, are also provided by the invention. Also provided by the invention are uses of the GSE-encoded peptides of the invention for the manufacture of medicaments for a variety of anticancer therapeutic applications.

Specific preferred embodiments of the present invention will become evident from the following more detailed description of certain preferred embodiments and the claims.

BRIEF DESCRIPTION OF THE DRAWINGS

FIG. 1 shows the structure of adaptors used for constructing a random fragment library from BCL2 cDNA, as described in Example 1. The 5' adaptor is comprised of the oligonucleotides SEH (SEQ ID No.:1) and ASEH (SEQ ID No.: 2). The HindIII site and the ATG codons in each reading frame are indicated by overlines. The 3' adaptor is comprised of the oligonucleotides SCB (SEQ ID No.:3) and ASCB (SEQ ID No.: 4). The ClaI site and the TGA codons in each reading frame are indicated by overlines.

FIG. 2 shows the nucleotide (SEQ ID No.: 5) and amino acid (SEQ ID No.: 6) sequences of the 2–7 GSE, the nucleotide (SEQ ID No. 7) and amino acid (SEQ ID No.: 8) sequences of the 2–25 GSE, and the nucleotide (SEQ ID No.: 9) and amino acid (SEQ ID No.: 10) sequences of the 6–2 GSE. Adaptor sequences are separated from BCL2 derived sequences by vertical lines.

DETAILED DESCRIPTION OF THE PREFERRED EMBODIMENTS

Figure 3:
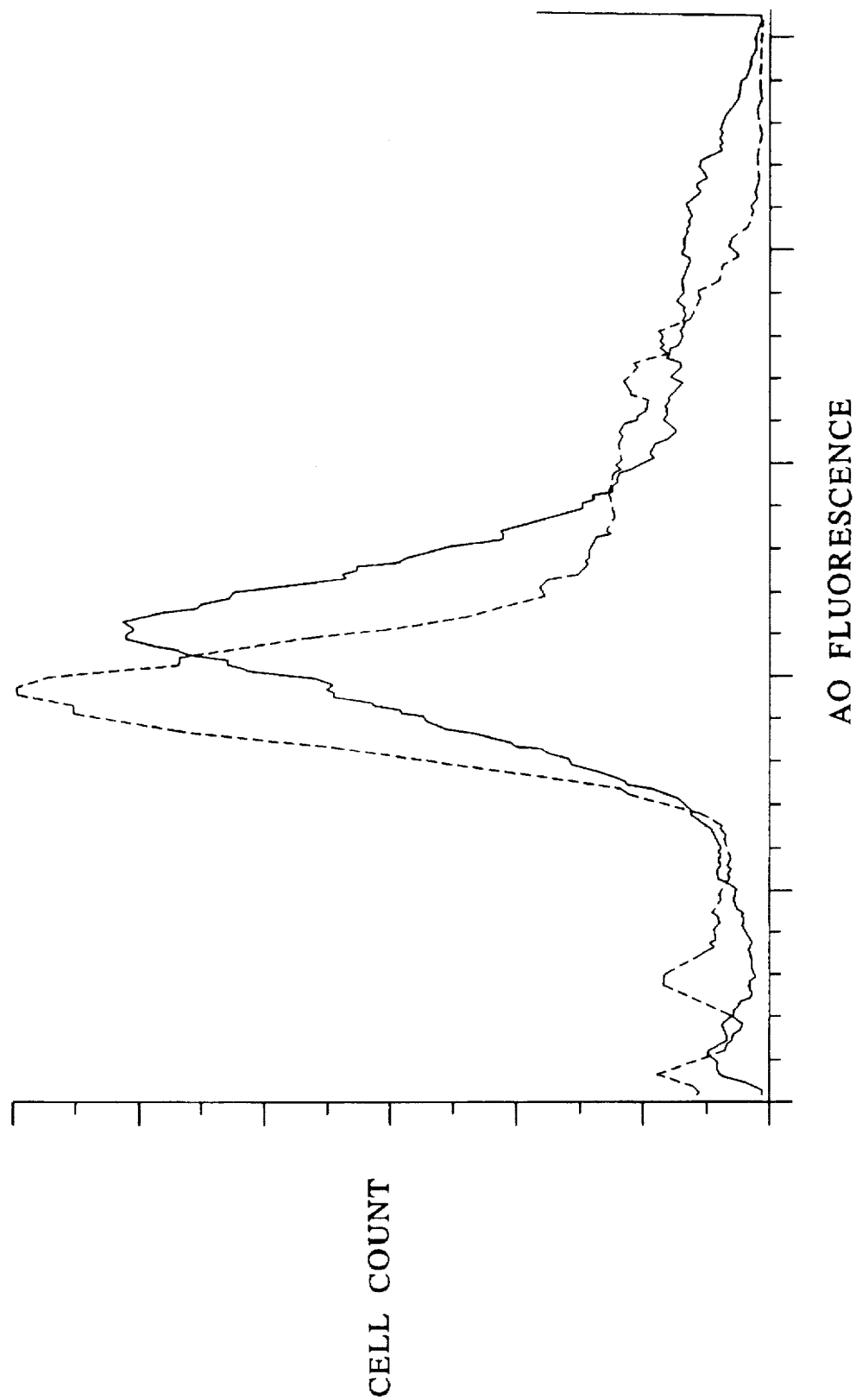
FIG. 3 shows a plot of fluorescence activated cell sorting (FACS) analysis of cell number versus acridine orange fluorescence for AA2 cells (■) and AA2 cells expressing the 2–25 GSE (- - - - -) after treatment with 2 μM dexamethasone.

The invention provides genetic suppressor elements (GSEs) that are fragments derived from a gene, BCL2, for reversing BCL2-mediated suppression of apoptosis in a mammalian cell. The invention provides nucleic acids encoding peptides having an amino acid sequence that is a portion of the BCL2 amino acid sequence. Particularly provided are GSEs identified herein as SEQ ID Nos.: 5, 7 and 9.

The invention also provides reagents and methods for sensitizing cancer cells to the apoptosis-producing effects of anticancer treatment modalities, and also provides reagents and methods having anticancer properties and characteristics in their own right.

The invention specifically provides genetic suppressor elements (GSEs) derived from mammalian, preferably human, BCL2 genes, and means for achieving an anticancer effect on neoplastic cells using such GSEs.

For the purposes of this invention, it will be understood that the term "BCL2 gene" encompasses any BCL2 gene from any species, particularly any mammalian species, and preferably from a rodent species (mouse or rat) or human BCL2 genes. The invention specifically is intended to contain within its scope all BCL2 genes and GSEs derived therefrom that are capable of producing sensitivity in a cancer cell to anticancer agents.

Anticancer agents that fall within the scope of this invention are intended to include but not be limited to ionizing and ultraviolet radiation, and chemotherapeutic drugs, including cytidine arabinoside, methotrexate, vincristine, etoposide, doxorubicin (Adriamycin), cisplatin, and dexamethasone.

The invention in particular provides GSEs derived from the cDNA of a human BCL2 gene isolated from a random fragment expression library, and isolated on the basis of its ability to produce apoptosis in human lymphoid cells after brief treatment with cytotoxic drugs.

The invention also provides methods for identifying BCL2 gene-derived GSEs for reversing BCL2-mediated suppression of apoptosis in a mammalian cell. Particularly provided are methods for identifying BCL2-derived GSEs that confer upon cancer cells sensitivity to cytotoxic drugs and other anticancer agents the effects of which are mediated at least in part by the induction of programmed cell death or apoptosis. The GSEs identified by this method will be homologous to a BCL2 gene. For purposes of the invention, the term "homologous to" a BCL2 gene has two different meanings, depending on whether the GSE acts through an antisense mechanism or antigene mechanism, or through a mechanism of interference at the protein level. In the former case, a GSE that is an antisense or antigene oligonucleotide or polynucleotide is homologous to a gene if it has a nucleotide sequence that hybridizes under physiological conditions to the gene or its mRNA transcript by Hoogsteen or Watson-Crick base-pairing. In the latter case, a GSE that interferes with a protein molecule is homologous to the gene encoding that protein molecule if it has an amino acid sequence that is the same as that encoded by a portion of the gene encoding the protein, or that would be the same, but for conservative amino acid substitutions. In either case, as a practical matter, whether the GSE is homologous to a gene is determined by assessing whether the GSE is capable of inhibiting or reducing the function of the gene; in particular, any BCL2 gene, preferably any rodent or human BCL2 gene, as disclosed herein.

The method according to this aspect of the invention comprises the step of screening a BCL2-specific cDNA or BCL2-specific genomic DNA random fragment expression library phenotypically to identify clones that confer resistance to a DNA damaging agent such as certain chemotherapeutic drugs. Preferably, the library of random fragments of BCL2-specific cDNA or BCL2-specific genomic DNA is cloned into a retroviral expression vector. In this preferred embodiment, retrovirus particles containing the library are used to infect cells and the infected cells are tested for the induction of apoptosis by brief treatment with an anticancer agent such as a cytotoxic drug. Preferably, the inserts in the library will range from about 50 basepairs (bp) to about 1000 bp. Any of a variety of techniques known in the art can be used to identify apoptotic cells, including, for example, fluorescence-activated cell sorting (FACS) of mixtures of apoptotic and non-apoptotic cells stained with dyes appropriate for discriminating therebetween. Once a population of cells that are apoptotic as a result of brief treatment with an anticancer agent has been isolated, the library clone(s) encoding the GSE is rescued from the cells. At this stage, the nucleotide sequence of the insert of the expression library may be determined; in clones derived from a BCL2 gene-specific cDNA random fragment expression library, the nucleotide sequence is expected to be homologous to a portion of the BCL2 gene cDNA nucleotide sequence. Alternatively, the rescued library clone may be further tested for its ability to confer sensitivity to anticancer agents such as chemotherapeutic drugs in additional transfection or infection and selection assays, prior to nucleotide sequence determination. Determination of the nucleotide sequence, of course, results in the identification of the GSE. This method is further illustrated in Example 1.

This invention also provides a method for obtaining BCL2 gene-derived GSEs having optimized suppressor activity. By screening a random fragment expression library made exclusively from BCL2 gene-specific fragments in a region of the protein sequence from which a GSE has been previously obtained, a much greater variety of GSEs derived specifically from such a functionally important region of the BCL2 gene can be obtained, compared with a random fragment library prepared from total BCL2 cDNA. Consequently, the likelihood of obtaining optimized GSEs, i.e., those BCL2-derived GSEs conferring an optimal level of sensitivity to a chemotherapeutic drug, is maximized using this approach.

This invention also provides GSEs, GSE-encoded peptides and methods for obtaining BCL2 gene-derived GSEs having a variant amino acid sequence that is altered, mutated or substituted at a position in the amino acid sequence of the GSE. In such embodiments, the amino acid or nucleotide encoded in the sequence of the GSE is different from the amino acid or nucleotide present in the sequence of the portion of the BCL2 gene from which the GSE is derived. Such variant GSEs and GSE-encoded peptides are intended to encompass naturally-occurring and man-made variants, including polymorphisms of any mammalian BCL2 gene sequence. Exemplary of such amino acid substitution variants are those disclosed herein in Examples 3 and 4. These disclosed variants have amino acid substitutions resulting in altered amino acid residues in the GSE-encoded peptides of the invention when compared with the amino acid residues found at equivalent positions in the human BCL2 amino acid sequence. These results demonstrate that amino acid substitution variants of the GSEs of the invention can be produced in which the BCL2 gene suppressing activity of their parent GSE is not abrogated. Such amino acid substitution variants of the GSEs and GSE-encoded peptides of the invention can be readily produced using methods well-known in the art, with a reasonable expectation of success in producing functional BCL2 gene inhibition.

Truncated versions of the human BCL2 protein have been reported in the prior art as having dominant negative mutant characteristics (see International Patent Application, Publication No. WO94/27426). In this reference is reported a BCL2 protein variant, termed BCL2-β, which is lacking the carboxyl-terminal, hydrophobic membrane-spanning domain of human BCL2. This protein has been found to inhibit BCL2 suppression of apoptosis, which the reference attributes to competition for binding to cellular effector molecules between the functional, membrane-associated BCL2 protein and the truncated BCL2-β variant. Such truncated variants of BCL2 can be distinguished from the GSEs and GSE-encoded peptides of the instant invention on the basis of, among other things, their size (being comprised of about 218 of the 239 amino acids of functional BCL2); their structure (being truncated substitution mutants of the native BCL2 protein, as contrasted with the nucleic acids and peptides comprising the GSEs and GSE-encoded peptides of the present invention); and their mechanism of action (which is thought to involve competition between the truncated variant and the native BCL2 protein for cellular effectors, compared with the instant disclosure (see Example 4) of inhibition of BCL2 gene expression by the GSE-encoded peptides of the present invention).

In addition to such methods, the invention provides peptides and oligonucleotides that are encoded by the BCL2-derived GSEs themselves, and synthetic embodiments thereof. Synthetic peptides according to the invention have amino acid sequences that correspond to amino acid sequences encoded by GSEs according to the invention. Synthetic oligonucleotides according to the invention have nucleotide sequences corresponding to the nucleotide sequences of GSEs according to the invention. Once a GSE has been discovered and sequenced, and its orientation is determined, it is straightforward to prepare an oligonucleotide corresponding to the nucleotide sequence of the GSE (for antisense-oriented GSEs) or a peptide corresponding to the amino acid sequence encoded by the GSE (for sense-oriented GSEs). In certain embodiments, such synthetic peptides or oligonucleotides may have the complete sequence encoded by the GSE or may have only part of the sequence present in the GSE, respectively. In certain other embodiments, the peptide or oligonucleotide may have only a portion of the GSE-encoded or GSE sequence. In such latter embodiments, undue experimentation is avoided by the observation that many independent GSE clones corresponding to a particular gene will have the same 5' or 3' terminus. This suggests that many GSEs have one critical endpoint, from which a simple walking experiment will determine the minimum size of peptide or oligonucleotide necessary to inhibit gene function. For peptides, functional domains as small as 6-8 amino acids have been identified for immunoglobulin binding regions. Thus, peptides or peptide mnimetics having these or larger dimensions can be prepared as GSEs. For antisense oligonucleotides, inhibition of gene function can be mediated by oligonucleotides having sufficient length to hybridize to their corresponding mRNA under physiological conditions. Generally, oligonucleotides having about 12 or more bases will fit this description. Preferably, such oligonucleotides will have from about 12 to about 100 nucleotides. The antisense oligonucleotides of this invention also do not comprise the translation initiator methionine codon of the cognate BCL2 gene from which the GSE is derived. As used herein, the term oligonucleotide includes modified oligonucleotides having nuclease-resistant internucleotide linkages, such as phosphorothioate, methylphosphonate, phosphorodithioate, phosphoramidate, phosphotriester, sulfone, siloxane, carbonate, carboxymethylester, acetamidate, carbamate, thioether, bridged phosphoramidate, bridged methylene phosphonate and bridged phosphorothioate internucleotide linkages. The synthesis of oligonucleotides containing these modified linkages is well known in the art (see, e.g., Uhlmann and Peyman, 1990, *Chem. Rev.* 90: 543–584; Schneider and Banner, 1990, *Tetrahedron Lett.* 31: 335). The term oligonucleotides also includes oligonucleotides having modified bases or modified ribose or deoxyribose sugars.

The invention also provides peptides and synthetic peptides that are encoded by GSEs against BCL2 gene activity. In particular, the invention provides a GSE-encoded peptide comprising a sequence of 28 amino acids (SEQ ID No.:6), derived from the BCL2 protein. Also, two mutant forms of this peptide, present in the clones 6-2 (SEQ ID No.:8) and 2-25 (SEQ ID No.:10), are also provided encoded in GSEs.

The invention also provides a method for isolating other biologically active variants of the GSEs and GSE-encoded peptides of the invention, and additional peptide GSEs from the BCL2 protein. Such GSEs can be isolated from random fragment libraries, prepared from a more limited segment of BCL2 cDNA in the region from which the GSE-encoded peptide designated as GSE 2-7 was derived. Such a library may advantageously be designed to contain shorter sequences than the original GSE, since shorter sequences, if active, may be easier to reproduce by chemical synthesis. Such a library may be generated, for example, by DNaseI digestion, Bal31 digestion, or random priming. Prior to selection, it may be advantageous to mutagenize the random fragment plasmid library, e.g., by propagating it in a mutator strain of *E. coli*. Additional GSEs can then be isolated using a selection scheme as described herein, for example, using a sensitive cell line-drug combination, such as MCF-7 cell line and vincristine. In addition to FACS-based approaches to the isolation of dead or dying cells, such cells can be isolated, for example, by their propensity to float in the media supernatant of a cell line that grows as a monolayer, or by isolating abnormal density cells by centrifugation-based techniques well-known in the art.

Specifically, amino acid substitution variants of the BCL2-derived peptide GSEs of the invention are provided, wherein the amino acid residue at one or more positions in each of the peptides is a residue different from the amino acid found in the corresponding position of the BCL2 domain from which that specific peptide is derived. Expressly encompassed within the scope of this invention are embodiments of the peptides of the invention having substitutions using any amino acid, whether naturally-occurring or atypical, wherein the resulting substituted peptide has anti-BCL2 biological activity as defined herein. Also expressly encompassed within the scope of this invention are such amino acid substitution variants where the substituted amino acid residue is an atypical amino acid, such as, for example, D-amino acids, modified or non-naturally-occurring amino acids, and altered amino acids to provide peptides with increased stability, potency or bioavailability. Topological variants are also encompassed by this invention, including linear and branched-chain embodiments and dimerized and cyclized embodiments of the GSE-encoded peptides of invention.

The invention provides methods for producing a genetic suppressor element encoding such variant peptides having an altered or substituted amino acid sequence. In the practice of such methods, a particular feature of each embodiment of the method is producing a plurality of mutated genetic suppressor elements in vivo or in vitro. In certain embodiments of such methods, this is accomplished by introducing a nucleic acid encoding such a peptide into a mutator strain of a host cell capable of replicating the nucleic acid. In other embodiments, variants, substitutions, and the like are produced by manipulation of the nucleic acid encoding such peptides in vitro, using techniques well-known in the art.

The invention also provides methods and reagents for inhibiting BCL2 gene expression, by modulating transcription of the BCL2 gene in a cell expressing the gene. In particular embodiments, sense-oriented GSEs are provided for this purpose.

The present invention also provides pharmaceutical compositions for oral, parenteral, topical and aerosol administration comprising BCL2-derived GSE-encoded peptides in amounts effective for inhibiting BCL2 function and increasing apoptosis in cells, for, inter alia, sensitizing cancer cells to the effects of chemotherapeutic treatment modalities, including cytotoxic drugs, radiation treatment, and other modalities whose effects on cancer cells are mediated by apoptosis, and in amounts effective for achieving an antineoplastic result per se using the GSE-encoded peptides of the invention. Particularly provided are compositions additionally comprising pharmaceutically acceptable diluents, adjuvants or carriers.

BCL2-derived GSEs of the invention may be generated and/or isolated by any means known in the art, including by means of recombinant production using well-accepted genetic engineering techniques, such as those disclosed in, for example, *Molecular Cloning: A Laboratory Manual*, 2d ed. (Sambrook et al, 1990, Cold Spring Harbor Laboratory Press, Cold Spring Harbor, N.Y.). Those of ordinary skill in the art are able to isolate or chemically synthesize a nucleic acid comprising a GSE or encoding the GSE-encoded peptides of the invention.

BCL2-derived GSE-encoded peptides of the invention may be generated and/or isolated by any means known in the art, including by means of recombinant production using well-accepted genetic engineering techniques (Sambrook et al., ibid.). Those of ordinary skill in the art are able to use isolated or chemically synthesized nucleic acids encoding the GSE-encoded peptides of the invention as components of recombinant expression constructs, wherein the nucleic acids are operably linked with transcriptional and/or translational control elements, whereby such recombinant expression constructs are capable of expressing the peptides of the invention in cultures of prokaryotic, or preferably eukaryotic cells, most preferably mammalian cells, transformed with such recombinant expression constructs. Such recombinant expression constructs, and cells carrying such constructs, are provided and explicitly encompassed by this invention.

Also provided by the invention are methods of using mammalian cells carrying recombinant expression constructs encoding the BCL2-derived GSEs of the invention to identify compounds that either induce or inhibit apoptosis by mechanisms that are independent of BCL2. In embodiments of such methods for identifying compounds that induce apoptosis, such compounds are contacted with cells expressing BCL2 (e.g., human breast adenocarcinoma MCF-7 cells) that do not carry a recombinant expression construct of the invention, and the degree, extent, and frequency of apoptosis compared with MCF-7 cells that carry a GSE-encoding recombinant expression construct and that are contacted with such compounds. In the alternative, BCL2-expressing cells are contacted with the compounds to be tested in the presence or absence of a GSE-encoded peptide of the invention, and apoptosis compared between each population of cells. In such experiments, it will be expected that compounds that induce apoptosis independently of BCL2 will cause apoptosis to an equivalent extent in cells with and without a GSE of the invention. In the absence of such an apoptosis-inducing compound, apoptosis will be expected to occur to a greater degree in BCL2-expressing cells carrying a recombinant expression construct encoding a GSE of the invention (or in such cells in the presence of a GSE-encoded peptide of the inventon) than those cells that do not comprise such a construct (or are not in contact with a GSE-encoded peptide).

Similarly, in embodiments of such methods for identifying compounds that inhibit apoptosis induced by various factors (e.g., radiation or cytotoxic drug treatments), such compounds are contacted with cells expressing BCL2 (e.g., MCF-7 cells) that do not carry a recombinant expression construct of the invention, and the degree, extent, and frequency of apoptosis arising upon administration of apoptosis-inducing factors is compared with MCF-7 cells that carry a GSE-encoding recombinant expression construct and that are contacted with such compounds. In alternatives to this embodiment of the methods of this aspect of the invention, BCL2-expressing cells are contacted with the compounds to be tested in the presence or absence of a GSE-encoded peptide of the invention, and apoptosis compared between each population of cells. In such experiments, it will be expected that compounds that inhibit apoptosis independently of BCL2 will inhibit apoptosis to an equivalent extent in cells with and without a GSE of the invention. In the absence of such an apoptosis-inhibiting compound, apoptosis will be expected to occur to a greater degree in BCL2-expressing cells carrying a recombinant expression construct encoding a GSE of the invention (or in such cells in the presence of a GSE-encoded peptide of the inventon) than those cells that do not comprise such a construct (or are not in contact with a GSE-encoded peptide).

Peptides of the invention may also be advantageously synthesized by any of the chemical synthesis techniques known in the art, particularly solid-phase synthesis techniques, for example, using commercially-available automated peptide synthesizers. Such peptides may also be provided in the form of fusion peptides or polypeptides, wherein the peptides comprising the combination are linked in a linear fashion one to another and wherein a GSE-encoded peptide sequence is present repeatedly in the peptide, with or without separation by "spacer" amino acids. Also provided are branched-chain combinations, wherein the component peptides are covalently linked via functionalities in amino acid sidechains of the amino acids comprising the peptides.

The peptides of this invention can be provided as recombinant hybrid fusion proteins comprising BCL2-derived GSE-encoded peptides and at least a portion of at least one other polypeptide, including, for example, virally-derived polypeptides such as the Tat protein of human immunodeficiency viruses (see Fawell et al., 1994, *Proc. Natl. Acad. Sci.* USA 91: 664–668; Pepinsky et al., 1994, *DNA & Cell Biol.* 13: 1011–1019). Such embodiments comprise fusion of the GSE-encoded peptide of the invention with Tat protein or specific peptide domains of the Tat protein, to provide embodiments of the GSE-encoded peptides of the invention that are efficiently taken up by mammalian cells. Such embodiments include also fusion peptides of polypeptides having the Tat protein activity of promoting efficient intracellular delivery.

Generally, those skilled in the art will recognize that peptides as described herein may be modified by a variety of chemical techniques to produce compounds having essentially the same activity as the unmodified peptide, and optionally having other desirable properties. For example, carboxylic acid groups of the peptide, whether carboxyl-terminal or sidechain, may be provided in the form of a salt of a pharmaceutically-acceptable cation or esterified to form a $C_1$–$C_6$ ester, or converted to an amide of formula $NR_1R_2$ wherein $R_1$ and $R_2$ are each independently H or $C_1$–$C_{16}$ alkyl, or combined to form a heterocyclic ring, such as 5- or 6-membered rings. Amino groups of the peptide, whether amino-terminal or sidechain, may be in the form of a pharmaceutically-acceptable acid addition salt, such as the HCl, HBr, acetic, benzoic, toluene sulfonic, maleic, tartaric and other organic salts, or may be modified to $C_1$–$C_{16}$ alkyl or dialkyl amino or further converted to an amide. Hydroxyl groups of the peptide sidechain may be converted to $C_1$–$C_{16}$ alkoxy or to a $C_1$–$C_{16}$ ester using well-recognized techniques. Phenyl and phenolic rings of the peptide sidechain may be substituted with one or more halogen atoms, such as fluorine, chlorine, bromine or iodine, or with $C_1$–$C_{16}$ alkyl, $C_1$–$C_{16}$ alkoxy, carboxylic acids and esters thereof, or amides of such carboxylic acids. Methylene groups of the peptide sidechains can be extended to homologous $C_2$–$C_4$ alkylenes. Thiols can be protected with any one of a number of well-recognized protecting groups, such as acetamido groups. Those skilled in the art will also recognize methods for introducing cyclic structures into the peptides of this invention to select and provide conformational constraints to the structure that result in enhanced binding and/or stability. For example, a carboxyl-terminal or amino-terminal cysteine residue can be added to the peptide, so that when oxidized the peptide will contain a disulfide bond, thereby generating a cyclic peptide. Other peptide cyclizing methods include the formation of thioethers and carboxyl- and amino-terminal amides and esters.

Peptidomimetic and organomimetic embodiments are also hereby explicitly declared to be within the scope of the present invention, whereby the three-dimensional arrangement of the chemical constituents of such peptido- and organomimetics mimic the three-dimensional arrangement of the peptide backbone and component amino acid sidechains in the peptide, resulting in such peptido- and organomimetics of the peptides of this invention having substantial biological activity. It is implied that a pharmacophore exists for the biological activity of the BCL2-derived GSE-encoded peptides of the invention. A pharmacophore is understood in the art as comprising an idealized, three-dimensional definition of the structural requirements for biological activity. Peptido- and organomimetics can be designed to fit each pharmacophore with current computer modelling software (computer aided drug design).

The administration of BCL2-derived GSE-encoded peptides is preferably accomplished with a pharmaceutical composition comprising the BCL2-derived peptide and a pharmaceutically acceptable diluent, adjuvant, or carrier. Effective doses of GSE-encoded peptides for sensitizing cancer cells to the apoptosis-producing effects of anticancer treatment modalities may be readily determined by those of skill in the art according to conventional parameters, each associated with the corresponding biological activity, including, for example, the size of the subject, the extent and nature of the neoplastic disease, the history of prior cancer treatment, and other clinically-relevant considerations. Similar determinations will be made by those of skill in this art for using the peptide embodiments of this invention for therapeutic uses envisioned and described herein.

In addition, introduction of a BCL2-derived GSE-encoded peptide of the invention into tumor cells can be combined with almost any clinically justifiable chemotherapeutic or radiotherapeutic protocol, with the expectation that the GSE should improve the therapeutic efficacy of such protocol.

Alternatively, any of the GSEs of the invention may be delivered to tumor cells through a gene therapy vector, such as a retroviral vector of the type disclosed herein, an adenovirus- or adeno-associated virus-based vector, or by non-viral transfection techniques that are well-known in the art.

Embodiments of the invention comprising medicaments can be prepared for oral administration, for injection, or other parenteral methods and preferably include conventional pharmaceutically acceptable carriers, adjuvents and counterions as would be known to those of skill in the art. The medicaments are preferably in the form of a unit dose in solid, semi-solid and liquid dosage forms such as tablets, pills, powders, liquid solutions or suspensions, and injectable and infusible solutions. Effective dosage ranges from about 100 µg/kg to about 10 mg/kg of body weight are contemplated.

The BCL2-derived GSEs provided by the invention can be used to sensitize tumor cells to anticancer agents. In addition to the anticancer drugs disclosed herein, the GSE effect can be expected to extend to other cytotoxic drugs and ionizing radiation, since BCL2 overexpression has been demonstrated to produce resistance to all of these agents (see Reed, 1994, ibid.). In addition, since BCL2 acts as an oncogene in non-Hodgkin's lymphomas and B-cell malignancies, such GSEs of the invention may be used in such tumors directly as an anticancer agent.

In addition, the BCL2-derived GSEs provided by the invention can be used in a variety of contexts to inhibit BCL2 gene expression or interfere with BCL2 gene product function. Uses for the GSEs and GSE-encoded peptides of the invention include treatment of cells harboring cytopathic viruses, such as human immunodeficiency virus (HIV-1 and HIV-2); treatment of embryonic, fetal, or developing cells, particularly developing hematopoietic cells, having apoptosis-related disorders or abnormalities in their developmental programming; treatment of neurological disorders related to inappropriate apoptosis; and other apoptosis-related diseases or disorders in an animal. Methods and reagents for inhibiting apoptosis-mediated senescence and cell death as well are provided by the invention.

Specific preferred embodiments of the present invention will become evident from the following more detailed description of certain preferred embodiments and the claims.

EXAMPLE 1

Generation of a Random Fragment Library In A Retroviral Vector from BCL2 cDNA

A random fragment library was prepared from BCL2 cDNA in a retroviral vector. The principle of GSE selection from the BCL2 target gene involved random fragmentation of a cDNA encoding the gene, followed by generation of a library carrying short random fragments of fragmented cDNA in an expression vector, the vector being capable of directing expression of either peptides or antisense RNAs from the inserted fragments. The random fragment library was then transduced into recipient cells that express BCL2, and the transduced cells selected for a phenotype expected to result from inhibition of the BCL2 gene. The integrated insert sequences were then recovered from the selected cells, recloned and tested for biological activity, to identify GSEs.

A BCL2 random fragment library was prepared from plasmid T3BCL-2ΔPst, carrying full-length BCL2 cDNA (917 bp) in pBluescript KS vector (3.0 kb) (a gift of Dr. Gordon Shore, McGill University). This plasmid had been derived from human BCL2 cDNA clone 58 (Seto et al., 1988, *EMBO J.* 7: 123-131), and carries BCL2 cDNA of clone 58 from the 5' end to the PstI site. The random fragment library was prepared as described in co-owned and copending U.S. Ser. Nos. 08/033,086 and 08/177,571, incorporated by reference herein.

Briefly, the entire T3BCL-2ΔPst plasmid was subjected to DNaseI digestion to generate random fragments ranging in size from 70–1000 basepairs (bp). Approximately 75% of these fragments were derived from the pBluescript vector DNA, and the remaining 25% of the fragments were specific for the BCL2 cDNA. The fragments were then blunt-ended using T4 DNA polymerase and the Klenow fragment of DNaseI. Thereafter, the fragments were ligated to two different synthetic adaptors, shown in FIG. 1, which were designed for directional cloning into a retroviral plasmid vector (pLNCX; Miller and Rosman, 1989, *Biotechniques* 7: 980–986) having unique HindIII (5') and ClaI (3') cloning sites. As shown in FIG. 1, the 5' adaptor contained a HindIII cloning site and ATG translation initiation codons in all three reading frames. The 3' adaptor contained TGA stop codons in all three frames and a ClaI cloning site.

After ligation with both adaptors, the random fragment population was amplified by polymerase chain reaction (PCR), using the SEH and ASCB oligonucleotides as primers. The PCR-amplified mixture was digested with HindIII and ClaI and then ligated into the pLNCX vector, which was pre-digested with both HindIII and ClaI. The result of this strategy was that only those fragments that were flanked by different adaptors could be cloned, and this provided for the appropriate orientation of the translation initiation and termination codons relative to the CMV promoter of the LNCX vector.

The ligated mixture was transformed into the INVαF' strain of *E. coli*, and approximately 70,000 independent colonies were generated. PCR analysis of 30 representative clone indicated that over 90% of the clones contained a recombinant construct. The DNA from these colonies was collected and purified by cesium chloride/ethidium bromide gradient centrifugation (see Sambrook et al., 1990, *Molecular Cloning: A Laboratory Manual*, Cold Spring Harbor Laboratory Press, N.Y. for a more detailed description of this purification scheme) for further characterization as described below.

EXAMPLE 2

Transduction Of A Retroviral Random Fragment Library Into Virus-Packaging Cells

In order to isolate GSEs specific for BCL2, DNA from the random fragment cDNA library produced as described in Example 1 was introduced into a human B-lymphoid cell line (AA2) which had been modified to produce the murine ecotropic retrovirus receptor (Albritton et al., 1989, *Cell* 57: 659–666); these cells were thus capable of being infected with the library in the form of a mixture of ecotropic recombinant retroviruses. Preliminarily, this cell line was tested for BCL2 mRNA expression using a RT-PCR assay (Noonan et al., 1990, *Proc. Natl. Acad. Sci. USA* 87: 7160–7164). In this assay, the following BCL2-specific primers were used for PCR:

GTGGCCTTCTTTGAGTTCGG (sense) and GGCTCA-GATAGGCACCCAGG (antisense) (SEQ ID Nos.:13 and 14, respectively). These primers were used for PCR with cellular cDNA derived as previously described (Noonan et al., ibid.) from 30 ng total cellular RNA. PCR was then performed using an amplification protocol comprising: a first cycle of PCR that was 3 min at 94° C., 1 min at 60° C. and 2 min at 72° C., followed by 27 cycles comprising 30 sec at 94° C., 30 sec at 60° C. and 1 min at 72° C. $\beta_2$-microglobulin sequences were amplified by 23 cycles of PCR as an internal control (Noonan et al., ibid.). This RT-PCR assay revealed the presence of detectable BCL2 mRNA in AA2 cells, suggesting that it was suitable as a recipient line for the selection of BCL2-derived GSEs.

To regenerate the retroviral library for transduction into AA2 cells, 15 μg of BCL2 random fragment plasmid library was transfected into $2 \times 10^6$ cells of an ecotropic packaging cell line BOSC23 (Pear et al., 1993, *Proc. Natl. Acad. Sci. USA* 90: 8392–8396) on a P100 tissue culture plate using calcium phosphate co-precipitation (see Sambrook et al., ibid.). 24 hours later, $2 \times 10^6$ AA2 cells were co-cultivated with BOSC23 in the presence of 4 μg/ml polybrene. After 24 hours of co-cultivation, the AA2 cells were collected by centrifugation and then again co-cultured with the transfected BOSC23 cells for another 24 hours in fresh media. Afterwards, AA2 cells were allowed to recover in fresh media for 48 hours and were then put into G418 selection for 7–10 days, to select for retroviral transductants.

AA2 cells carrying LNCX retroviral clones encoding GSEs specific for BCL2 were detected and isolated as follows. The cellular phenotype expected from the inhibition of BCL2 was an increased amount of active cell death (ACD, also known as apoptosis) upon exposure to cytotoxic treatments. In order to select for increased ACD, AA2 infectants were exposed to very low doses of ACD-inducing agents and then screened for ACD utilizing fluorescence-activated cell sorter (FACS). For these assays, two DNA staining dyes, Acridine Orange (AO) and Propidium Iodide (PI), were used to detect cells undergoing ACD. Acridine Orange is a dye that stains DNA green and RNA red. Cells that were undergoing apoptosis showed diminished AO DNA staining, and these cells can be collected by FACS sorting (Compton et al., 1988, *Endocrinology* 122: 2158–2164). PI, on the other hand, is commonly used to stain dead cells, based on the loss of their membrane integrity (Ross et al., 1989, *Cancer Res.* 49: 3776–3782).

The initial selection involved exposing AA2 cells carrying either the library or the LNCX vector alone (a negative control) to 2 μM dexamethasone for 40 hours. Both populations were then stained with AO and tested by FACS analysis. After dexamethasone treatment, about 1% of the control cells were found to be undergoing ACD as detected by decreased AO staining, while approximately 5% of library-carrying cells showed decreased AO staining characteristic for ACD. This "apoptotic" population was isolated by flow sorting; approximately $1 \times 10^5$ cells were recovered. These cells were lysed and genomic DNA was extracted. This DNA was used to recover the inserts from integrated proviruses by PCR, using the following vector-derived primers that flank the cloning site:

CCTGGAGACGCCATCCAC (sense) and AGCTAGCT-TGCCAAACCTA (antisense) (SEQ ID Nos.: 15 and 16, respectively). Electrophoretic analysis of the PCR products indicated very strong enrichment for a distinct band corresponding to an insert approximately 80 bp in size. These PCR products were purified, restriction enzyme digested with HindIII and ClaI and then recloned into LNCX for further testing.

An alternate selection protocol was also used. This protocol involved exposing the library-carrying and the control cells to 20 nM vincristine for 1.5 hours. After exposure to vincristine, the cells were extensively washed and allowed to recover in the drug-free media for 17 hours. The cells were then stained with 10 μg/mL PI and analyzed on FACS. Cells that were strongly reactive with PI (defined as dead cells) and cells that showed moderate PI reactivity (operationally defined as dying cells) were sorted separately. The genomic DNA was extracted and subjected to PCR as described above. In three separate and independent populations, the same band corresponding to an approximately 80 bp-insert was highly enriched both in the "dying" and in the "dead" cell populations. These PCR products were also purified and recloned in LNCX.

EXAMPLE 3

Structural Characterization of BCL2-Derived GSEs

Clones carrying the enriched LNCX insert of approximately 80-bp were identified through PCR as described above and sequenced using conventional dideoxynucleotide sequencing technology (see Sambrook et al., ibid). 15 clones were completely sequenced, and 13 of them were found to have the same sequence (shown in FIG. 2). Each of these clones contained a sense-oriented 81 bp fragment of BCL2 cDNA, located between the 5' and 3' adaptors. Coincidentally, the last 2 bp of the 5' adaptor and the first 2 bp of the 3' adaptor are identical to the BCL2 sequences flanking this fragment, thus extending the region of identity between the clones and BCL2 cDNA to 85 bp (FIG. 2). This clone sequence, if translated in the reading frame of the BCL2 protein, encodes a peptide of 32 amino acids, wherein the first two and the last two residues are derived from the adaptor sequence, and the internal 28 amino acids correspond to a fragment of the BCL2 protein (residues 92–119). This fragment represents 11.7% of the total BCL2 protein length of 239 amino acids Two single-base altered mutant sequences have been identified among the 15 clones. The mutation in one of the clones (clone 2–25) alters the corresponding amino acid from methionine to threonine at position 24 of the peptide, and the other clone (clone 6–2) carries a serine to cysteine substitution at position 28 (FIG. 2).

This peptide sequence of 28 amino acids of the BCL2 protein found in the selected clones, does not overlap with any of the three conserved domains of BCL2 that have been implicated in interactions between members of the BCL2 family (Sato et al., 1994, Proc. Natl. Acad. Sci. USA 91: 9238–9242). However, this region includes a heptapeptide sequence YRRDFAE (underlined in FIG. 2), which was recently shown to be involved in the interactions between BCL2 and three newly discovered proteins of as yet unknown function (termed Nip1, Nip2 and Nip3; Boyd et al., 1994, Cell 79: 341–351).

To measure the degree of enrichment achieved as described above for the selected fragment, colony hybridization assays were carried out with plasmid libraries derived from each of four PCR-amplified populations. The first population was obtained after dexamethasone selection, the second and the third populations after independent vincristine selections, and the fourth population was the original non-selected BCL2 fragment library. These populations were screened with both the whole BCL2 cDNA probe and a probe corresponding to the selected fragment. As shown in Table I below, there was a very strong enrichment for this element in all three independently selected populations relative to the original library.

TABLE I

| Enrichment for BCL2 GSE in independent selections | | |
|---|---|---|
| Selection | BCL2+ | GSE+ |
| None (original library) | 47/176 (26.7%) | 4/176 (2.3%) |
| Dexamethasone | 62/176 (35.2%) | 61/176 (34.7) |
| Vincristine-1 | 93/176 (52.8%) | 46/176 (26.1%) |
| Vincristine-2 | 88/176 (50.0%) | 46/176 (26.1%) |

EXAMPLE 4

Drug-Sensitizing Activities of BCL2 GSE

Figure 4:
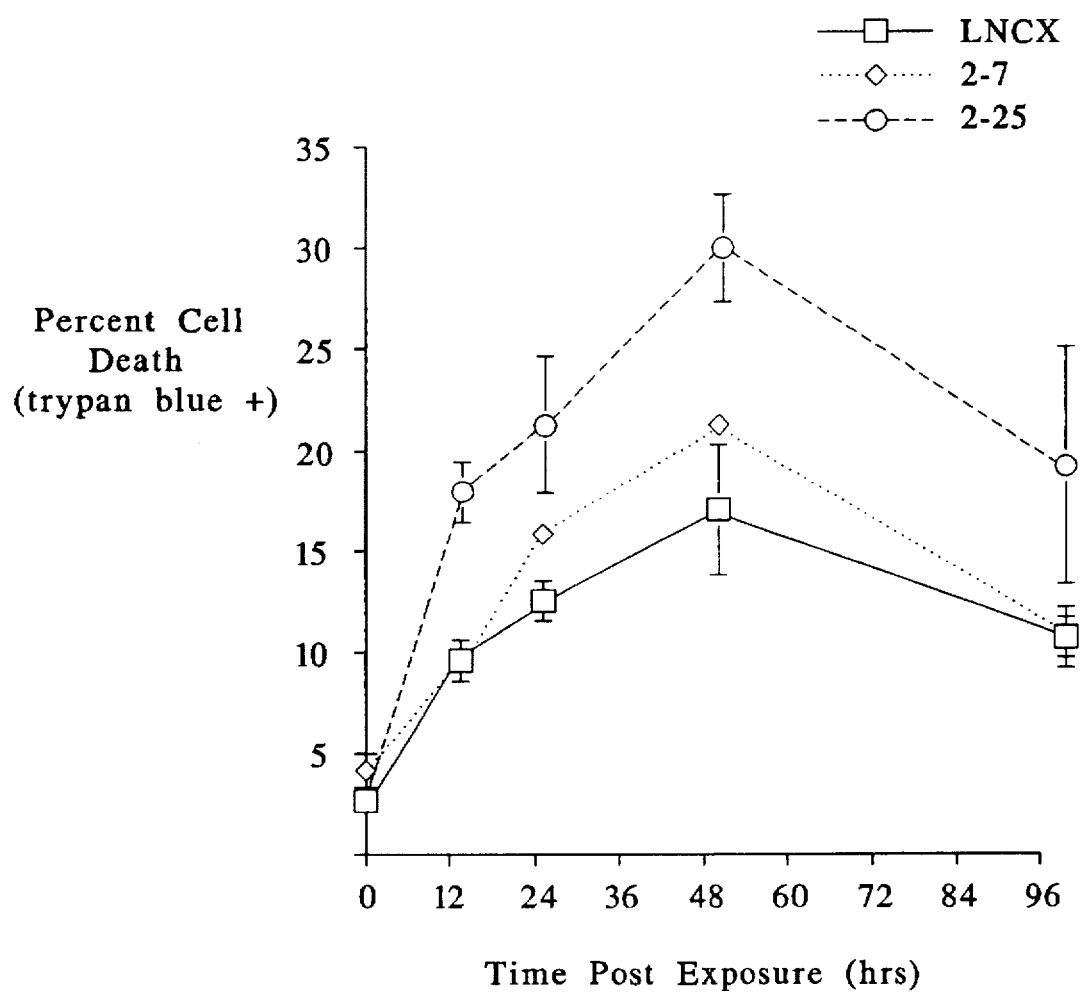
FIG. 4 shows a plot of percent cell death versus time of exposure to vincristine in cells infected with control pLNCX vector (-□-) and the LNCX vector carrying the 2–7 GSE (-♦-) or the 2–25 GSE (-O-).

The wild-type and mutant BCL2 GSEs, recloned in the LNCX vector, were tested for the ability to promote ACD induced by cytotoxic drugs. A representative wild-type clone, called 2–7, and a mutant clone 2–25 were each introduced into AA2 cells by retroviral transduction. Following G418 selection, these cells were then tested for their effects on these cells after treatment with dexamethasone or vincristine. Cells were treated for varying times with cytotoxic drugs and then analyzed by FACS analysis after staining with AO and PI. As shown in FIG. 3, the clone 2–25 GSE produced an approximately two-fold increase in the percentage of cells undergoing apoptosis, as indicated by AO staining, while the effect of the 2–7 was either very small or undetectable by this assay. 2–25 also produced an approximately 2-fold increase in the percentage of dead cells (estimated by trypan blue or PI staining) that arose following 1.5 hr treatment with 20 nM vincristine, while 2–7 produced a weaker effect in this type of assay (results shown in FIG. 4). Another mutant clone, 6–2 (FIG. 2), was also tested in the latter assay and showed an intermediate level of sensitization between 2–7 and 2–25.

Figure 5:
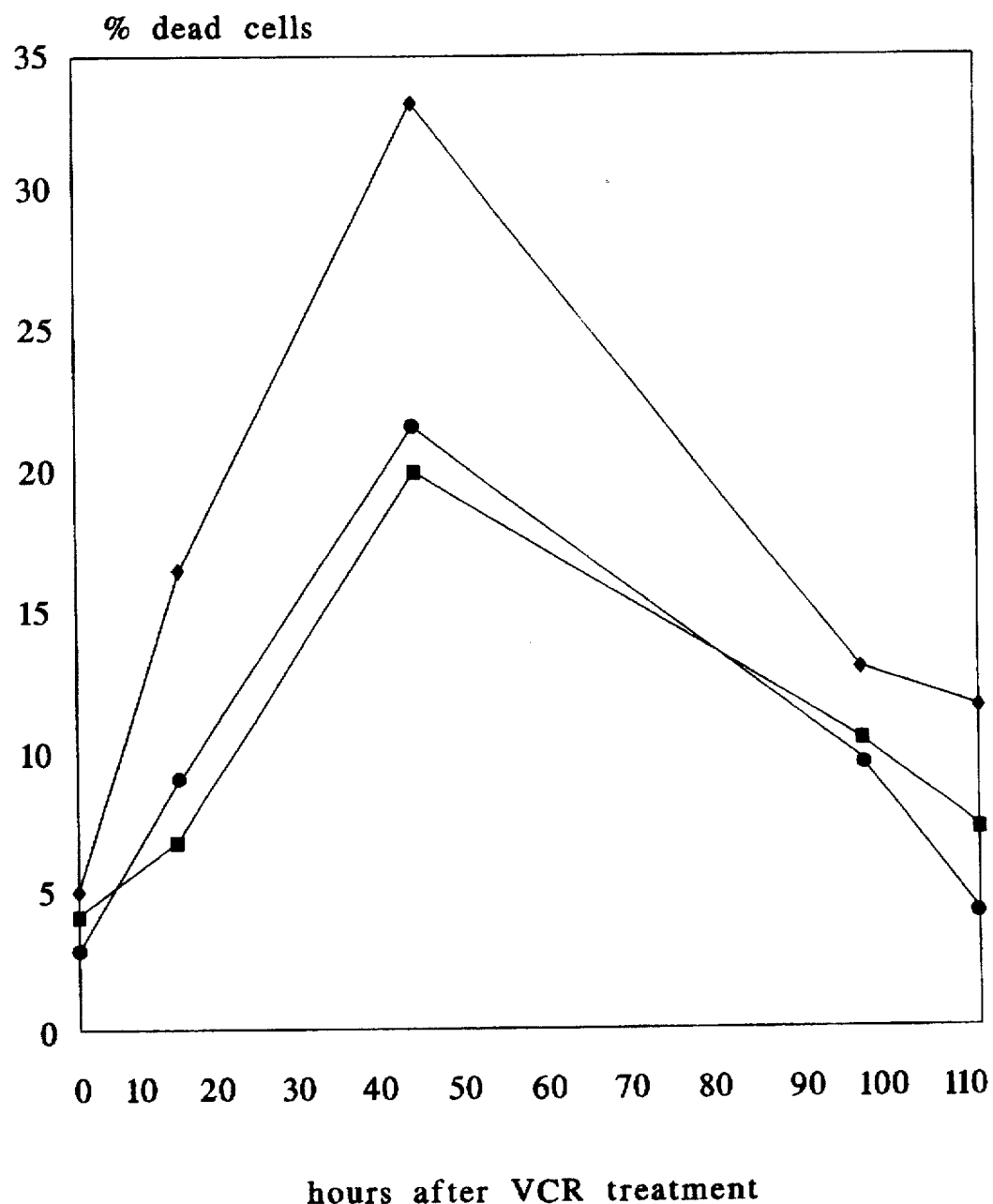
FIG. 5 shows a plot of the percent dead cells versus time after vincristine treatment in cultures of AA2 cells infected with control LNCX virus (-□-), and 2–25 GSE expressed in a single translation-initiator codon construct (-*-) and the 2–25 GSE expressed in a translation frameshift initiator construct (-■-).

This assay utilizing vincristine was also used to demonstrate that the effect of the mutant 2–25 GSE was mediated through the BCL2-derived peptide. In these experiments, two modified versions of the 2–25 clone were generated by PCR using different mutated versions of the original 5' adaptor (as shown in FIG. 2). The first adaptor (single ATG adaptor) preserved only one of three original ATG initiation codons; the remaining ATG provided for translation of the insert in the reading frame of BCL2. The second adaptor (frameshift adaptor) carried a singe-base frameshift mutation which allowed for only five amino acids (unrelated to BCL2) to be translated from the single ATG codon. These clones were introduced into AA2 by retroviral transduction. Following G418 selection, the cells were treated with vincristine. As shown in FIG. 5, the construct corresponding to 2–25 with a single ATG codon sensitized AA2 cells to the cytotoxic effects of exposure to vincristine. In contrast, the frameshift construct had no effect. This result indicated that the 2–25 GSE exerted its genetic suppressor effect through the BCL2-derived peptide.

The 2–25 (mutant) and 2–7 (wild-type) GSE clones were also tested for their activity in other types of leukemia- and solid-tumor derived cell lines (in addition to AA2), including leukemia cells (K562 and HL60), colon carcinoma (SW480) and breast carcinoma (MCF-7). RT-PCR analysis of BCL2 RNA indicated that, among these cell lines, the lowest levels of endogenous BCL2 expression were present in AA2 and K562 lines, and the highest levels in HL60 and MCF-7 cells. In these experiments, cells transduced with a BCL2-derived GSE were briefly exposed to one of a variety of cytotoxic agents, then cultured in the absence of the cytotoxic agent for 5–8 days. In some cases, cell survival relative to untreated cells was determined by a plating efficiency colony assay, while in other cases, the appearance and percentage of dead cells was detected by staining with vital dyes such as trypan blue and propidium iodide at difference time points after drug treatment, and quantitatively analyzed by, for example, FACS analysis.

Figure 6:
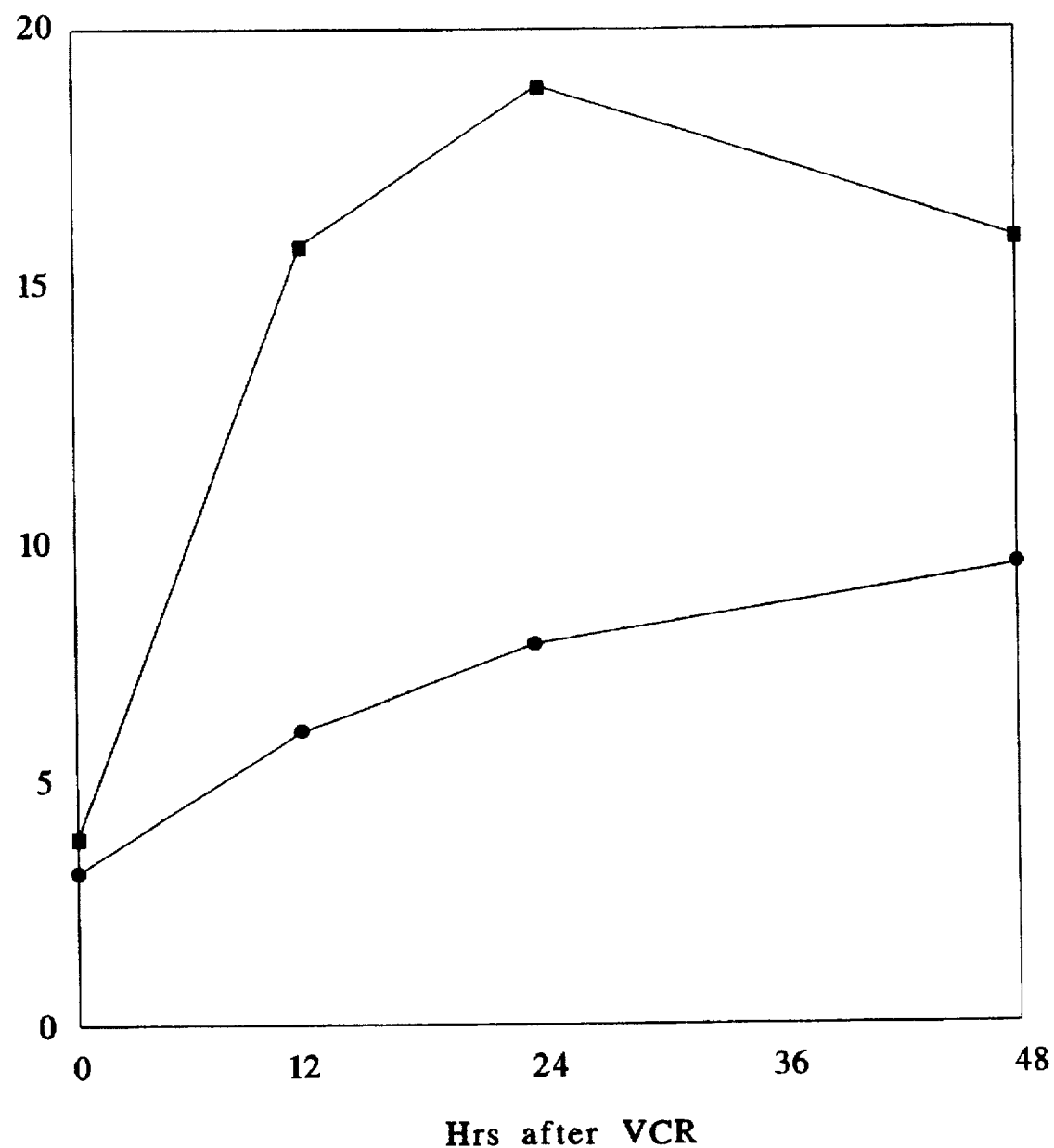
FIG. 6 shows a plot of percent cell death versus time after vincristine treatment in HL60 leukemia cells infected with LNCX virus (-■-) or virus encoding the 2–25 GSE (-+-).
Figure 7:
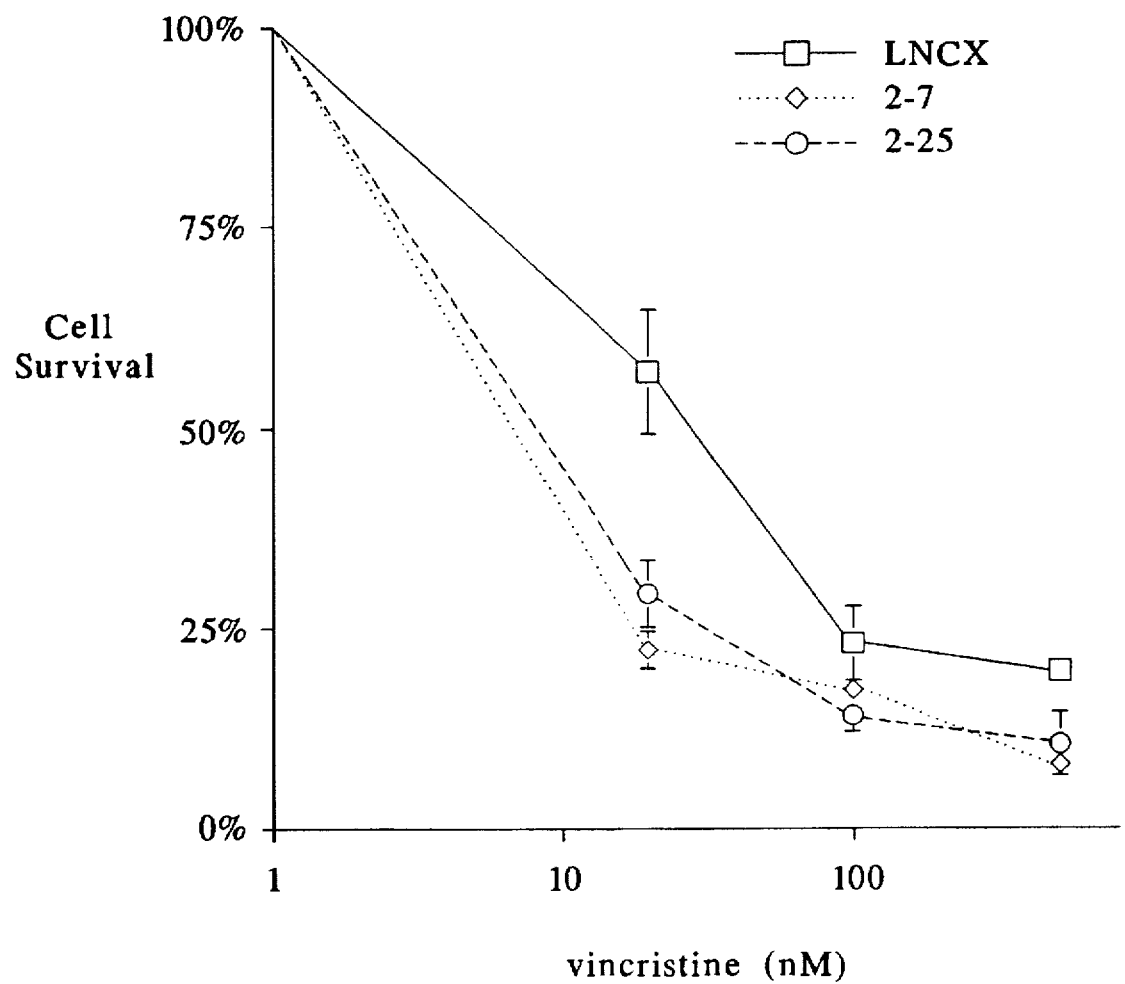
FIG. 7 shows a plot of percent cell survival versus vincristine concentration in SW480 colon carcinoma cells infected with LNCX virus (-□-) or encoding the 2–7 GSE (-♦-) or the 2–25 GSE (-O-).
Figure 8:
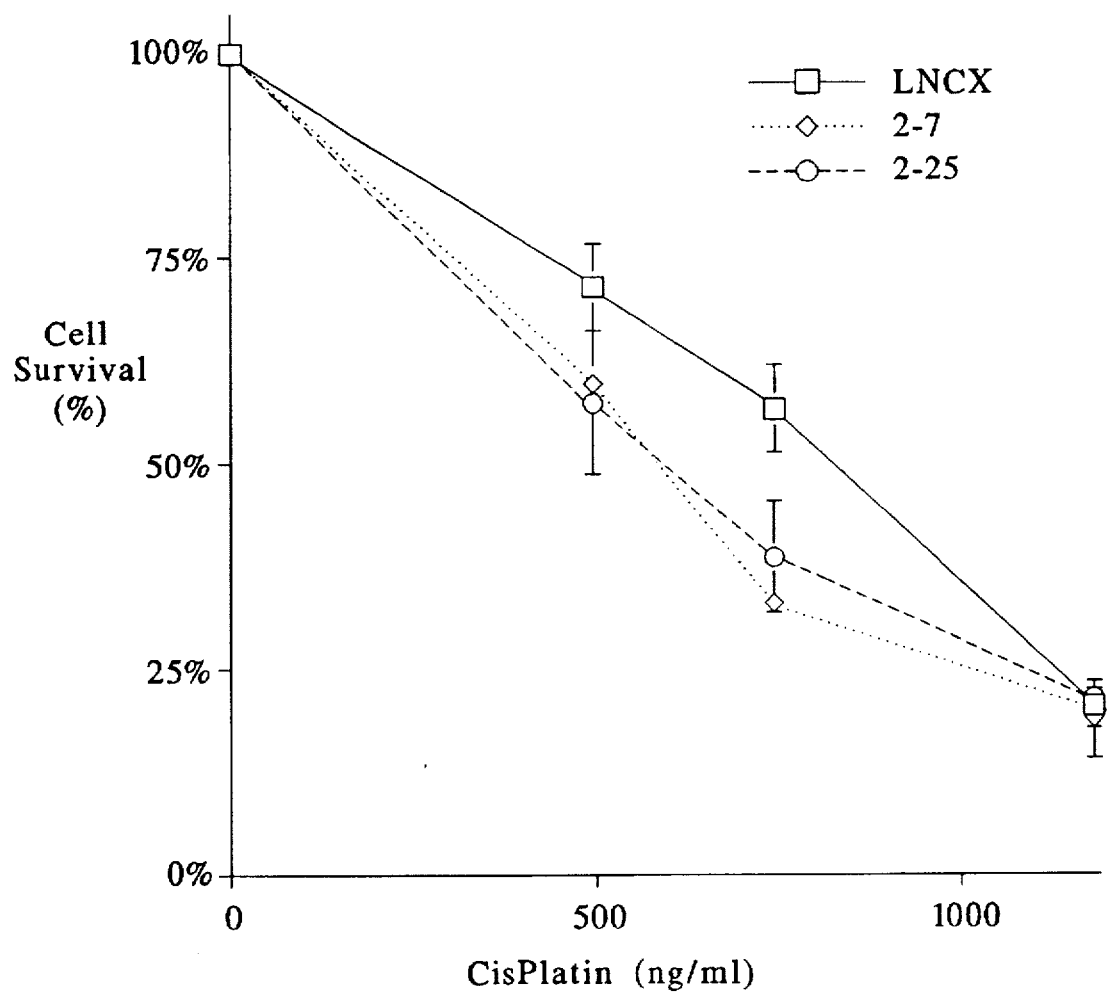
FIG. 8 shows a plot of percent cell survival versus cisplatin concentration in SW480 colon carcinoma cells infected with LNCX virus (-□-) or encoding the 2–7 GSE (-♦-) or the 2–25 GSE (-O-).
Figure 9:
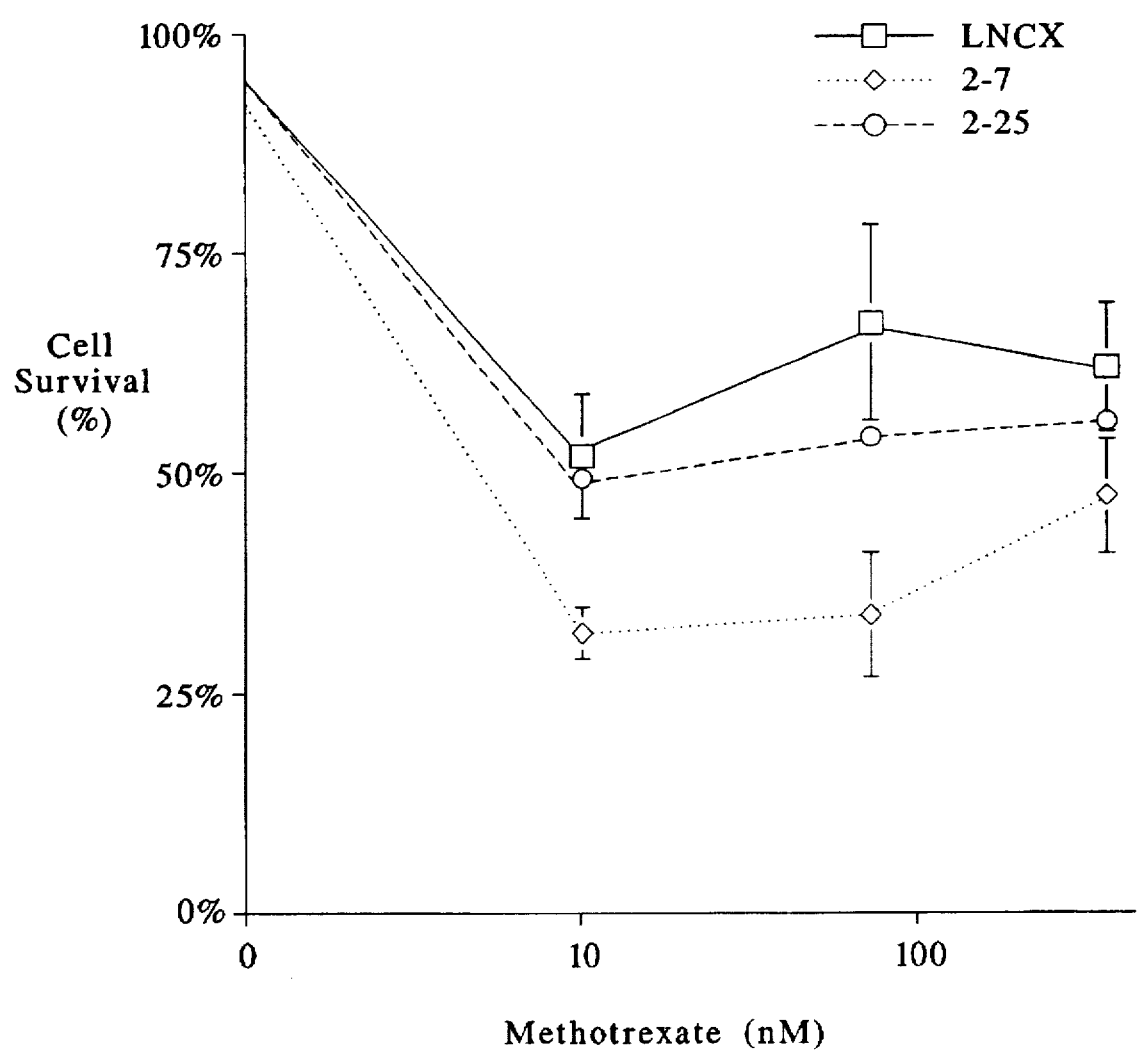
FIG. 9 shows a plot of percent cell survival versus methotrexate concentration in SW480 colon carcinoma cells infected with LNCX virus (-□-) or encoding the 2–7 GSE (-♦-) or the 2–25 GSE (-O-).
Figure 10:
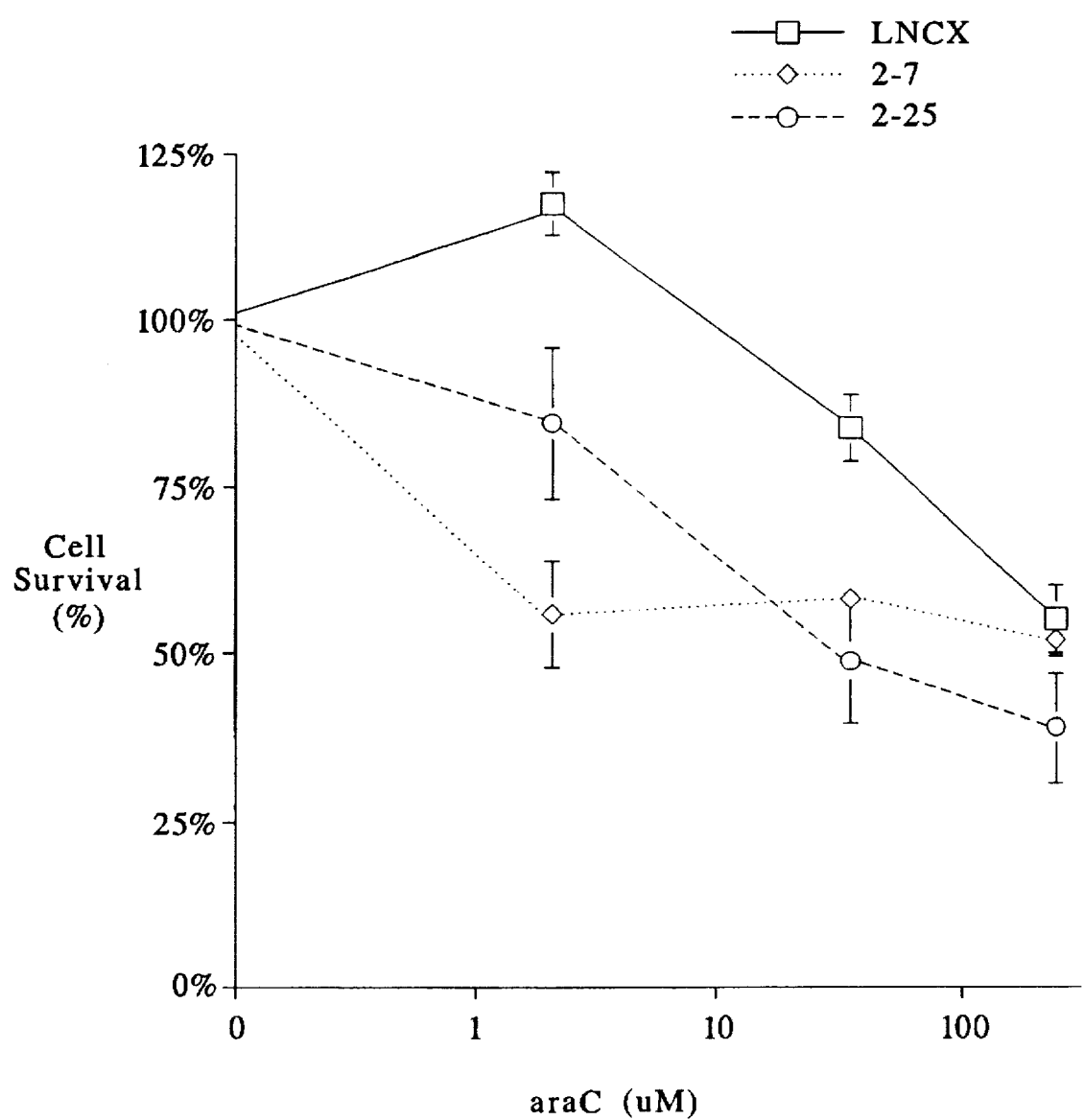
FIG. 10 shows a plot of percent cell survival versus cytidine arabinoside concentration in SW480 colon carcinoma cells infected with LNCX virus (-□-) or encoding the 2–7 GSE (-♦-) or the 2–25 GSE (-O-).

2–25 and 2–7 GSE clones were each introduced into these cell lines by retroviral transduction via an amphotropic packaging cell line (PA317; Bender et al., 1987, *J. Virol.* 61: 1639–1646). Neither the 2–25 nor 2–7 GSE showed detectable effect on vincristine-induced cells death in K562, suggesting that BCL2 does not play a significant role in the drug response of these cells. In contrast, the 2–25 GSE induced pronounced sensitization of HL-60 leukemia cells to 20 nM vincristine (FIG. 6). In SW480 colon carcinoma, both 2–7 and 2–25 clones induced moderate sensitization to varying concentrations of vincristine (FIG. 7), cisplatin (FIG. 8), methotrexate (FIG. 9) and cytidine arabinoside (FIG. 10), detectable by plating efficiency assays for drug cytotoxicity.

Figure 11:
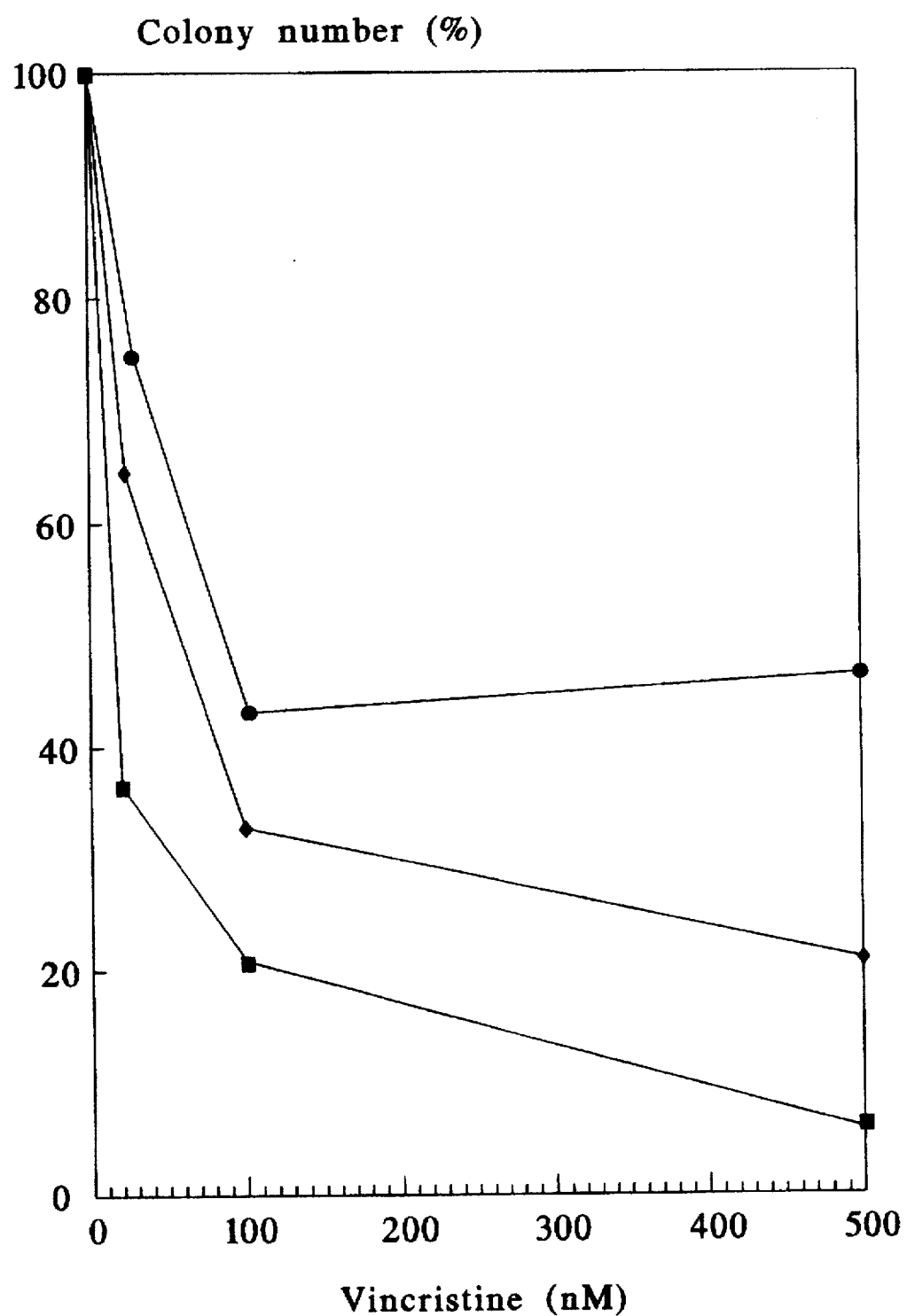
FIG. 11 shows a plot of percent cell survival versus vincristine concentration in MCF-7 breast carcinoma cells infected with LNCX virus (-■-) or encoding the 2–7 GSE (-*-) or a full-length BCL2 antisense mRNA (-+-).
Figure 12:
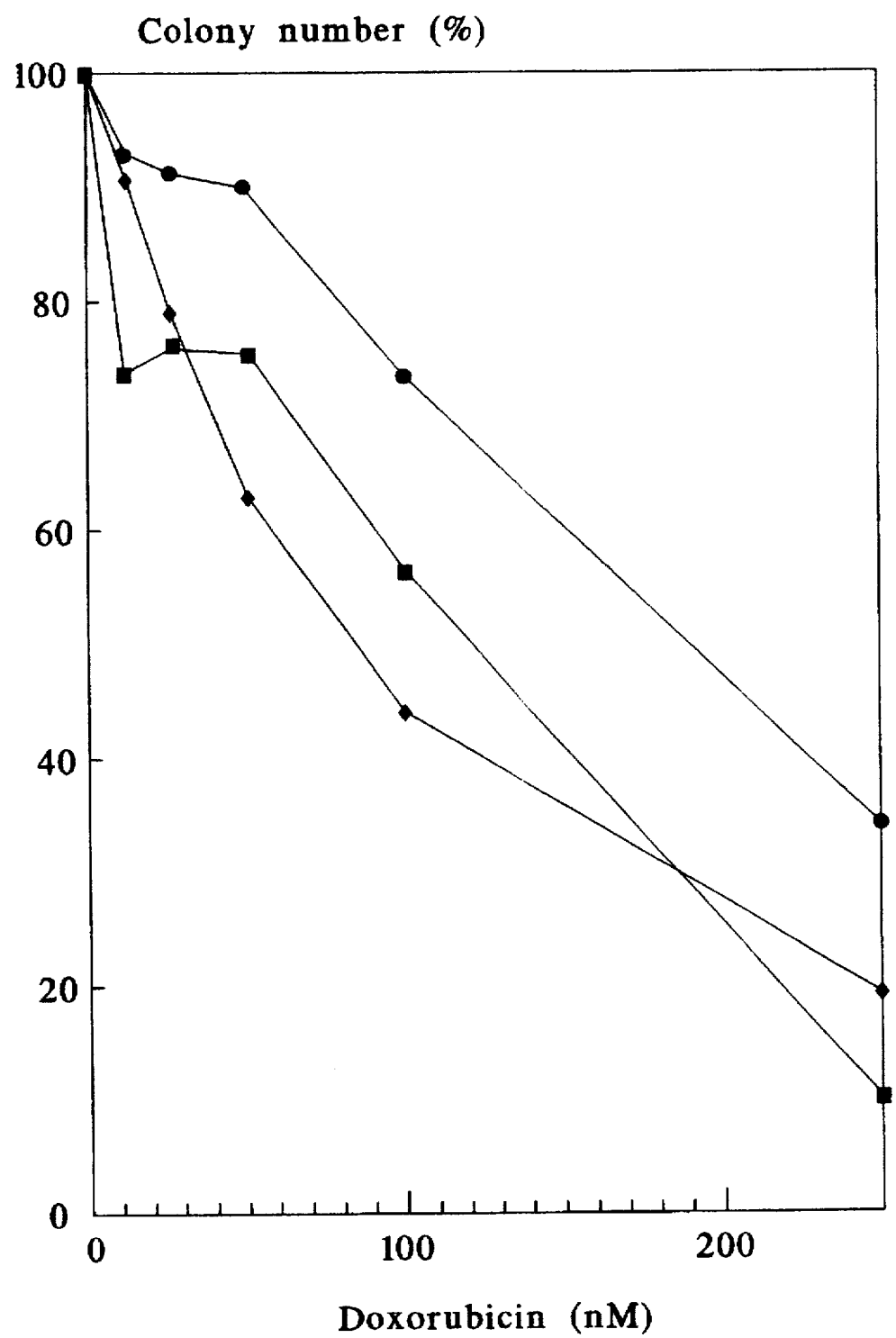
FIG. 12 shows a plot of percent cell survival versus doxorubicin concentration in MCF-7 breast carcinoma cells infected with LNCX virus (-■-) or encoding the 2–7 GSE (-*-) or a full-length BCL2 antisense mRNA (-+-).
Figure 13:
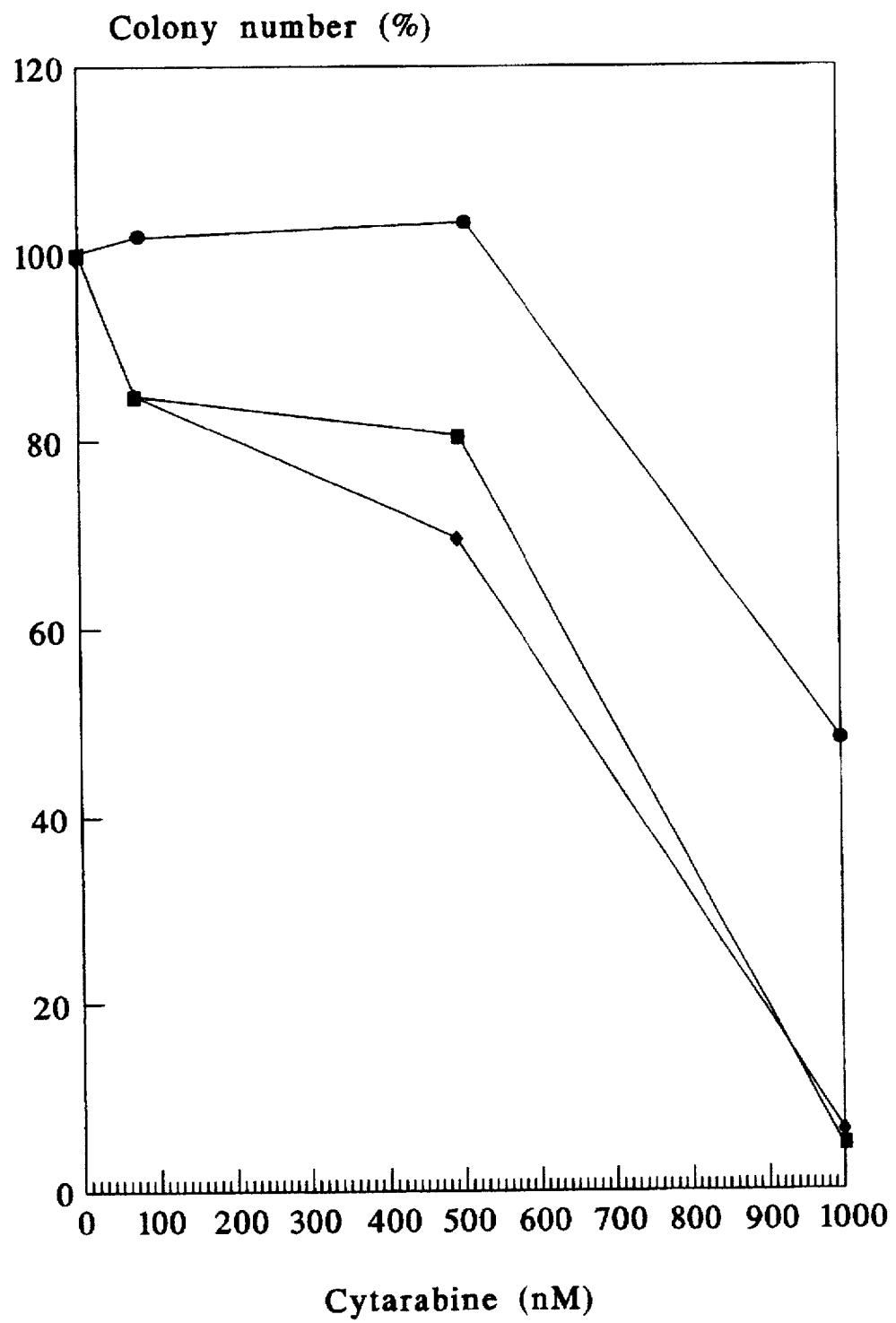
FIG. 13 shows a plot of percent cell survival versus cytidine arabinoside concentration in MCF-7 breast carcinoma cells infected with LNCX virus (-■-) or encoding the 2–7 GSE (-*-) or a full-length BCL2 antisense mRNA (-+-).

The strongest effect of the 2–7 GSE clone was observed in MCF-7 breast carcinoma cells. The introduction of the 2–7 GSE into these cells sensitized them to vincristine by approximately an order of magnitude (shown in FIG. 11). The 2–7 GSE clone also sensitized MCF-7 cells to doxorubicin, detected after exposure for 2.5 hrs, followed by 5 days recovery in drug-free media (FIG. 12) and cytidine arabinoside (FIG. 13). For comparison, the sensitizing capacity of a LNCX BCL2 full length antisense construct was determined. The sensitizing effect of the 2–7 GSE clone was found (see FIGS. 11–13) to be as strong (in some experiments) or stronger (in other experiments) than that of the LNCX-based, full-length BCL2 antisense RNA construct (compare, Kitada et al., *Antisense Res. Develop.* 4: 71–79). In contrast to the 2–7 GSE clone, the mutant 2–25 clone (which appeared to have more activity than 2–7 in AA2 cells) sensitized MCF-7 cells in some but not all experiments, and, even when active, appeared to have a lesser effect than the 2–7 GSE.

The above results have indicated that the BCL2-derived peptide, encoded by the 2–7 clone, and the mutant versions of this peptide, encoded by the 6–2 and 2–25 clones, act as GSEs. The BCL2-derived GSEs sensitize tumor cells to anticancer drugs. Among several types of tested leukemia- and solid tumor-derived cell lines, the strongest effect was observed in a breast carcinoma cell line, suggesting that chemosensitization by such GSEs may be particularly applicable to breast cancer.

EXAMPLE 5

Inhibition of BCL2 Gene Expression by Peptide GSEs

BCL2 gene expression levels in MCF-7 cells expressing BCL2-derived GSEs were determined using a quantitative RT-PCR assay (see Noonan et al., ibid.). MCF-7 cells that were transduced with the insert-free LNCX retrovirus, this retrovirus expressing BCL2 antisense RNA, and retroviruses carrying each of the 2–7 and 2–25 GSEs described above were tested in these assays. The results of these assays are shown in FIG. 14.

Figure 14:
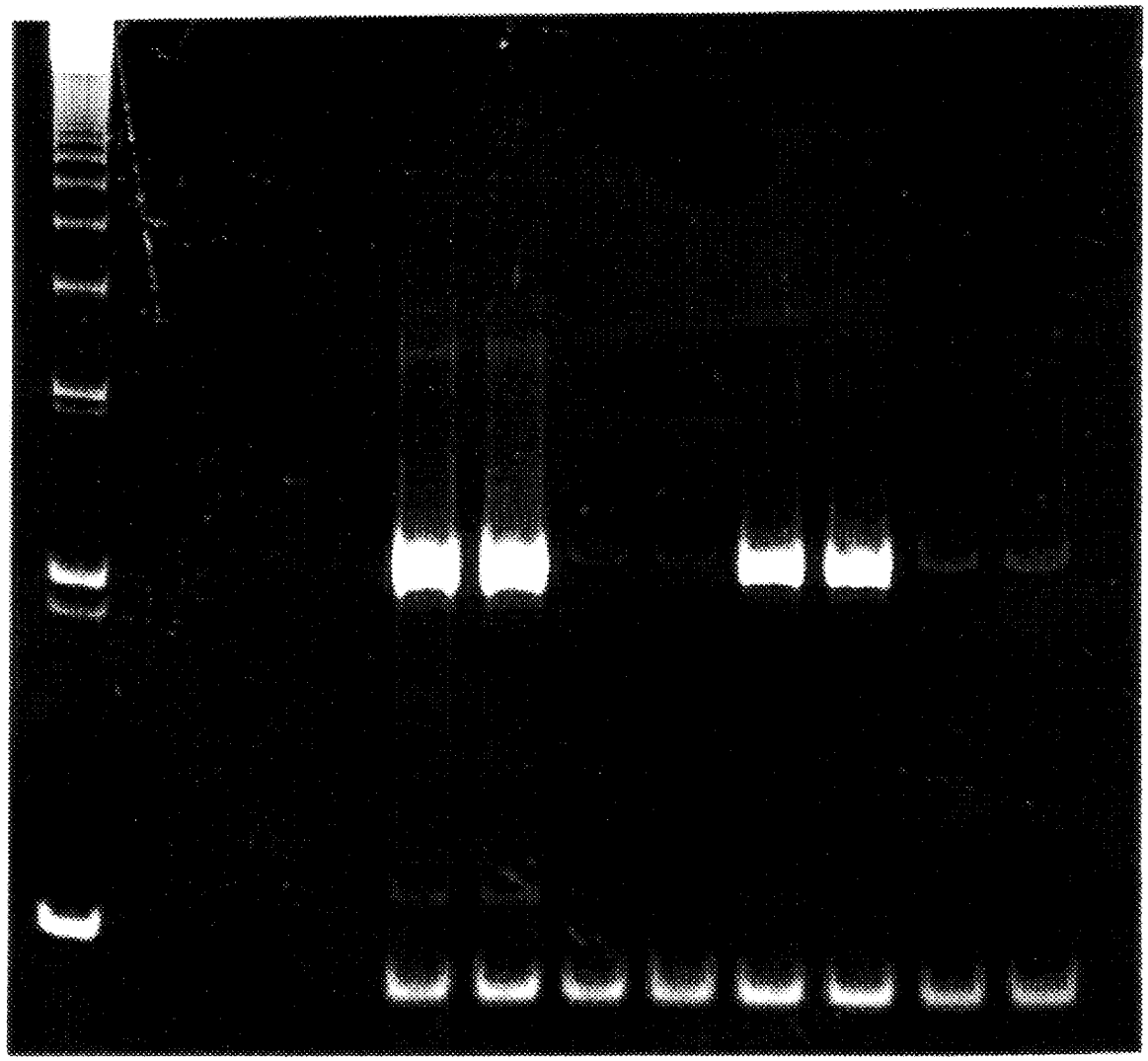
FIG. 14 shows the results of reverse transcriptase-polymerase chain reaction (RT-PCR) assay on MCF-7 cells infected with LNCX vector, the 2–7 GSE, the 2–25-GSE and a full-length antisense mRNA. Labeled bands represent PCR amplification products specific for $\beta_2$-microglobulin ($\beta_2$M) and BCL2.

As shown in FIG. 14, BCL2 mRNA expression is almost completely ablated in GSE-expressing cells. Down-regulation of BCL2 mRNA was also detected in GSE-containing AA2 and HL-60 cells (data not shown). These results demonstrated that these BCL2-derived GSEs act by inhibiting BCL2 gene expression.

The observed effect of BCL2 protein fragments on the steady-state RNA levels is unexpected and indicates the existence of a BCL2 regulatory mechanism that has not been appreciated in the prior art. Analysis of this mechanism is likely to provide additional tools for manipulating the process of programmed cell death. The magnitude of BCL2 RNA inhibition by the 2–7 clone in MCF-7 cells indicates that this GSE has close to maximal achievable efficacy in BCL2 inhibition through this mechanism.

It should be understood that the foregoing disclosure emphasizes certain specific embodiments of the invention and that all modifications or alternatives equivalent thereto are within the spirit and scope of the invention as set forth in the appended claims.

We claim:

1. A sense-oriented genetic suppressor element of which encodes an amino acid sequence identified by a Sequence ID Number selected from the group consisting of SEQ ID Nos.: 6, 8 and 10.

2. A genetic suppressor element according to claim 1 wherein the amino acid sequence of the peptide optionally encodes a methionine residue, a glutamic acid residue, or the dipeptides Met-Glu or Glu-Met at the amino terminus of the peptide.

3. A genetic suppressor element according to claim 1 wherein the amino acid sequence of the peptide optionally encodes a serine residue, an aspartic acid residue, or the dipeptides Ser-Asp or Asp-Ser at the carboxyl terminus of the peptide.

4. A genetic suppressor element according to claim 1 wherein the amino acid sequence of the peptide optionally encodes a methionine residue, a glutamic acid residue, or the dipeptides Met-Glu or Glu-Met at the amino terminus of the peptide, and wherein the amino acid sequence of the peptide optionally encodes a serine residue, an aspartic acid residue, or the dipeptides Ser-Asp or Asp-Ser at the carboxyl terminus of the peptide.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i v ) ANTI-SENSE: NO ( x i ) SEQUENCE DESCRIPTION: SEQ ID NO:1:

TACCGAATTC AAGCTTATGG ATGGATG    27

( 2 ) INFORMATION FOR SEQ ID NO:2:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (ii) MOLECULE TYPE: cDNA (iv) ANTI-SENSE: YES (xi) SEQUENCE DESCRIPTION: SEQ ID NO:2:

CATCCATCCA TAAGCTTGAA TTC                                                                           23

(2) INFORMATION FOR SEQ ID NO:3:

(i) SEQUENCE CHARACTERISTICS:
                (A) LENGTH: 23 base pairs
                (B) TYPE: nucleic acid
                (C) STRANDEDNESS: single
                (D) TOPOLOGY: linear (ii) MOLECULE TYPE: cDNA (iv) ANTI-SENSE: NO (xi) SEQUENCE DESCRIPTION: SEQ ID NO:3:

TGAGTGAGTG AATCGATGGA TCC                                                                           23

(2) INFORMATION FOR SEQ ID NO:4:

(i) SEQUENCE CHARACTERISTICS:
                (A) LENGTH: 27 base pairs
                (B) TYPE: nucleic acid
                (C) STRANDEDNESS: single
                (D) TOPOLOGY: linear (ii) MOLECULE TYPE: cDNA (iv) ANTI-SENSE: YES (xi) SEQUENCE DESCRIPTION: SEQ ID NO:4:

TATAGGATCC ATCGATTCAC TCACTCA                                                                       27

(2) INFORMATION FOR SEQ ID NO:5:

(i) SEQUENCE CHARACTERISTICS:
                (A) LENGTH: 84 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:5:

GTGGTCCACC TGACCCTCCG CCAGGCCGGC GACGACTTCT CCCGCCGCTA CCGCCGCGAC                                    60

TTCGCCGAGA TGTCCAGCCA GCTG                                                                          84

(2) INFORMATION FOR SEQ ID NO:6:

(i) SEQUENCE CHARACTERISTICS:
                (A) LENGTH: 28 amino acids
                (B) TYPE: amino acid
                (D) TOPOLOGY: linear (ii) MOLECULE TYPE: peptide (v) FRAGMENT TYPE: internal (xi) SEQUENCE DESCRIPTION: SEQ ID NO:6:

```
        Val Val His Leu Thr Leu Arg Gln Ala Gly Asp Asp Phe Ser Arg Arg
        1             5                   10                  15

Tyr Arg Arg Asp Phe Ala Glu Met Ser Ser Gln Leu
                    20              25
```

( 2 ) INFORMATION FOR SEQ ID NO:7:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

```
GTGGTCCACC TGACCCTCCG CCAGGCGGC GACGACTTCT CCCGCCGCTA CCGCCGCGAC      60

TTCGCCGAGA CGTCCAGCCA GCTG                                           84
```

( 2 ) INFORMATION FOR SEQ ID NO:8:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:8:

```
        Val Val His Leu Thr Leu Arg Gln Ala Gly Asp Asp Phe Ser Arg Arg
        1             5                   10                  15

Tyr Arg Arg Asp Phe Ala Glu Thr Ser Ser Gln Leu
                    20              25
```

( 2 ) INFORMATION FOR SEQ ID NO:9:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
GTGGTCCACC TGACCCTCCG CCAGGCGGC GACGACTTCT CCCGCCGCTA CCGCCGCGAC      60

TTCGCCGAGA TGTCCTGCCA GCTG                                           84
```

( 2 ) INFORMATION FOR SEQ ID NO:10:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:10:

```
        Val Val His Leu Thr Leu Arg Gln Ala Gly Asp Asp Phe Ser Arg Arg
        1             5                   10                  15

Tyr Arg Arg Asp Phe Ala Glu Met Ser Cys Gln Leu
                    20              25
```

( 2 ) INFORMATION FOR SEQ ID NO:11:

( i ) SEQUENCE CHARACTERISTICS:
        ( A ) LENGTH: 760 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 21..740

( x i ) SEQUENCE DESCRIPTION: SEQ ID NO:11:

```
TTGCTTTTCC TCTGGGAAGG ATG GCG CAC GCT GGG AGA ACG GGG TAC GAC         50
                     Met Ala His Ala Gly Arg Thr Gly Tyr Asp
                      1               5                  10

AAC CGG GAG ATA GTG ATG AAG TAC ATC CAT TAT AAG CTG TCG CAG AGG       98
Asn Arg Glu Ile Val Met Lys Tyr Ile His Tyr Lys Leu Ser Gln Arg
             15                  20                  25

GGC TAC GAG TGG GAT GCG GGA GAT GTG GGC GCC GCG CCC CCG GGG GCC      146
Gly Tyr Glu Trp Asp Ala Gly Asp Val Gly Ala Ala Pro Pro Gly Ala
             30                  35                  40

GCC CCC GCA CCG GGC ATC TTC TCC TCC CAG CCC GGG CAC ACG CCC CAT      194
Ala Pro Ala Pro Gly Ile Phe Ser Ser Gln Pro Gly His Thr Pro His
             45                  50                  55

CCA GCC GCA TCC CGC GAC CCG GTC GCC AGG ACC TCG CCG CTG CAG ACC      242
Pro Ala Ala Ser Arg Asp Pro Val Ala Arg Thr Ser Pro Leu Gln Thr
         60                  65                  70

CCG GCT GCC CCC GGC GCC GCC GCG GGG CCT GCG CTC AGC CCG GTG CCA      290
Pro Ala Ala Pro Gly Ala Ala Ala Gly Pro Ala Leu Ser Pro Val Pro
 75                  80                  85                  90

CCT GTG GTC CAC CTG GCC CTC CGC CAA GCC GGC GAC GAC TTC TCC CGC      338
Pro Val Val His Leu Ala Leu Arg Gln Ala Gly Asp Asp Phe Ser Arg
                 95                 100                 105

CGC TAC CGC GGC GAC TTC GCC GAG ATG TCC AGC CAG CTG CAC CTG ACG      386
Arg Tyr Arg Gly Asp Phe Ala Glu Met Ser Ser Gln Leu His Leu Thr
            110                 115                 120

CCC TTC ACC GCG CGG GGA CGC TTT GCC ACG GTG GTG GAG GAG CTC TTC      434
Pro Phe Thr Ala Arg Gly Arg Phe Ala Thr Val Val Glu Glu Leu Phe
            125                 130                 135

AGG GAC GGG GTG AAC TGG GGG AGG ATT GTG GCC TTC TTT GAG TTC GGT      482
Arg Asp Gly Val Asn Trp Gly Arg Ile Val Ala Phe Phe Glu Phe Gly
            140                 145                 150

GGG GTC ATG TCT GTG GAG AGC GTC AAC CGG GAG ATG TCG CCC CTG GTG      530
Gly Val Met Ser Val Glu Ser Val Asn Arg Glu Met Ser Pro Leu Val
155                 160                 165                 170

GAC AAC ATC GCC CTG TGG ATG ACT GAG TAC CTG AAC CGG CAC CTG CAC      578
Asp Asn Ile Ala Leu Trp Met Thr Glu Tyr Leu Asn Arg His Leu His
                175                 180                 185

ACC TGG ATC CAG GAT AAC GGA GGC TGG GAT GCC TTT GTG GAA CTG TAC      626
Thr Trp Ile Gln Asp Asn Gly Gly Trp Asp Ala Phe Val Glu Leu Tyr
                190                 195                 200

GGC CCC AGC ATG CGG CCT CTG TTT GAT TTC TCC TGG CTG TCT CTG AAG      674
Gly Pro Ser Met Arg Pro Leu Phe Asp Phe Ser Trp Leu Ser Leu Lys
            205                 210                 215

ACT CTG CTC AGT TTG GCC CTG GTG GGA GCT TGC ATC ACC CTG GGT GCC      722
Thr Leu Leu Ser Leu Ala Leu Val Gly Ala Cys Ile Thr Leu Gly Ala
    220                 225                 230

TAT CTG AGC CAC AAG TGAAGTCAAC ATGCCTGCCC CAA                        760
Tyr Leu Ser His Lys
235                 240
```

( 2 ) INFORMATION FOR SEQ ID NO:12:

( i ) SEQUENCE CHARACTERISTICS:
        ( A ) LENGTH: 239 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Met Ala His Ala Gly Arg Thr Gly Tyr Asp Asn Arg Glu Ile Val Met
 1           5                  10                  15
Lys Tyr Ile His Tyr Lys Leu Ser Gln Arg Gly Tyr Glu Trp Asp Ala
             20                  25                  30
Gly Asp Val Gly Ala Ala Pro Pro Gly Ala Ala Pro Ala Pro Gly Ile
         35                  40                  45
Phe Ser Ser Gln Pro Gly His Thr Pro His Pro Ala Ala Ser Arg Asp
     50                  55                  60
Pro Val Ala Arg Thr Ser Pro Leu Gln Thr Pro Ala Ala Pro Gly Ala
 65                  70                  75                  80
Ala Ala Gly Pro Ala Leu Ser Pro Val Pro Pro Val Val His Leu Ala
                 85                  90                  95
Leu Arg Gln Ala Gly Asp Asp Phe Ser Arg Arg Tyr Arg Gly Asp Phe
                100                 105                 110
Ala Glu Met Ser Ser Gln Leu His Leu Thr Pro Phe Thr Ala Arg Gly
            115                 120                 125
Arg Phe Ala Thr Val Val Glu Glu Leu Phe Arg Asp Gly Val Asn Trp
        130                 135                 140
Gly Arg Ile Val Ala Phe Phe Glu Phe Gly Gly Val Met Ser Val Glu
145                 150                 155                 160
Ser Val Asn Arg Glu Met Ser Pro Leu Val Asp Asn Ile Ala Leu Trp
                165                 170                 175
Met Thr Glu Tyr Leu Asn Arg His Leu His Thr Trp Ile Gln Asp Asn
            180                 185                 190
Gly Gly Trp Asp Ala Phe Val Glu Leu Tyr Gly Pro Ser Met Arg Pro
        195                 200                 205
Leu Phe Asp Phe Ser Trp Leu Ser Leu Lys Thr Leu Leu Ser Leu Ala
    210                 215                 220
Leu Val Gly Ala Cys Ile Thr Leu Gly Ala Tyr Leu Ser His Lys
225                 230                 235
```

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

GTGGCCTTCT TGAGTTCGG                                                      20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single

```
        ( D ) TOPOLOGY: linear ( i i ) MOLECULE TYPE: cDNA ( i v ) ANTI-SENSE: YES ( x i ) SEQUENCE DESCRIPTION: SEQ ID NO:14:

GGCTCAGATA GGCACCCAGG                                                        20

( 2 ) INFORMATION FOR SEQ ID NO:15:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:15:

CCTGGAGACG CCATCCAC                                                          18

( 2 ) INFORMATION FOR SEQ ID NO:16:

( i ) SEQUENCE CHARACTERISTICS:
            ( A ) LENGTH: 19 base pairs
            ( B ) TYPE: nucleic acid
            ( C ) STRANDEDNESS: single
            ( D ) TOPOLOGY: linear ( i i ) MOLECULE TYPE: cDNA ( i v ) ANTI-SENSE: YES ( x i ) SEQUENCE DESCRIPTION: SEQ ID NO:16:

AGCTAGCTTG CCAAACCTA                                                         19
```